United States Patent

Yoshida et al.

[11] Patent Number: 5,563,169
[45] Date of Patent: Oct. 8, 1996

[54] TRICYCLIC HETEROCYCLIC COMPOUND

[75] Inventors: Akira Yoshida; Kozo Oda; Takashi Kasai; Teiichiro Koga; Kazuo Hasegawa, all of Tokyo, Japan

[73] Assignee: Sankyo Company, Limited, Tokyo, Japan

[21] Appl. No.: 204,420

[22] PCT Filed: Sep. 11, 1992

[86] PCT No.: PCT/JP92/01164

§ 371 Date: Jul. 6, 1994

§ 102(e) Date: Jul. 6, 1994

[87] PCT Pub. No.: WO93/03740

PCT Pub. Date: Apr. 3, 1993

[30] Foreign Application Priority Data

Sep. 13, 1991 [JP] Japan .................... 3-234834

[51] Int. Cl.$^6$ ...................... A61K 31/35; C07D 311/90
[52] U.S. Cl. ........................ 514/454; 549/388; 549/392; 549/60; 549/27; 549/26
[58] Field of Search ................... 549/26, 27, 60, 549/388, 392; 514/455, 454, 444, 437

[56] References Cited

U.S. PATENT DOCUMENTS 4,489,090 12/1984 DeVries et al. .................... 549/26
4,999,373 3/1991 Trivedi .......................... 514/437

*Primary Examiner*—Nicky Chan
*Attorney, Agent, or Firm*—Frishauf, Holtz, Goodman, Langer & Chick, P.C.

[57] ABSTRACT

Constitution

Tricyclic heterocyclyl compounds having a general formula (I):

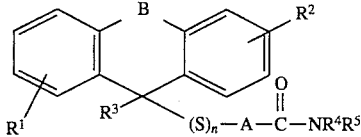

wherein: $R^1$ and $R^2$ each represents H, a lower alkyl or lower alkoxy group, a halogen atom or halogeno-lower alkyl; $R^3$ represents H or a lower alkyl group; $R^4$ represents a substituted phenyl or naphthyl group; $R_5$ represents H or a lower alkyl group; A represents a lower alkylene group; B represents an —O— or —S— group; and n is 0–1.

Effect

The compounds have an excellent activity in the inhibition of acyl-CoA: cholesterol acyltransferase (ACAT) and are useful for the treatment and prophylaxis of atherosclerosis.

21 Claims, No Drawings

TRICYCLIC HETEROCYCLIC COMPOUND

This application is a 371 of PCT/JP92/01164 filed Sep. 11, 1992.

TECHNICAL FIELD

The present invention relates to tricyclic heterocyclyl compounds which have excellent activity in the inhibition of acyl-CoA: cholesterol acyltransferase.

BACKGROUND ART

Atherosclerosis is an important cause of ischemic cardiac insufficiency such as angina, myocardial infarction and the like. It has been considered that a major cause of atherosclerosis is the accumulation of cholesterol esters by foam cells which are present under the endodermis cell layer of blood vessels.

Inhibitors of acyl-CoA: cholesterol acyltransferase (hereinafter referred as ACAT) inhibit the synthesis of cholesterol esters in the foam cells and they diminish the accumulation of cholesterol esters, thereby inhibiting the formation and development of atherosclerosis caused by the accumulation of cholesterol esters.

It has also been established that atherosclerosis is linked with hypercholesterolemia. Cholesterols in food are absorbed as free cholesterol in the intestinal mucosal cell tract, esterified by ACAT and then enter the blood. Therefore, an inhibitor of ACAT will also prevent a rise in the cholesterol concentration in the blood by inhibiting the absorption of food cholesterol into the blood.

For this reason, compounds which are active in the inhibition of ACAT are useful for the treatment and prophylaxis of atherosclerosis.

Tricyclic heterocyclyl compounds which inhibit ACAT are known and, for example, a compound having the formula:

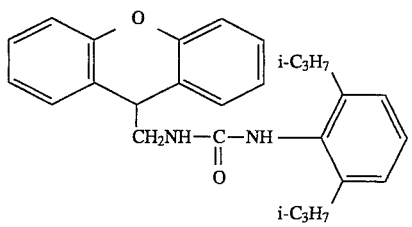

has been disclosed in Japanese Patent Kokai Application No. Hei 2-6457.

However, it is still desired to develop a therapeutic agent having more potent activity.

DISCLOSURE OF INVENTION

The present inventors have studied the synthesis of a series of tricyclic heterocyclyl compounds and the pharmacological activity thereof for many years. As a result, they have discovered that tricyclic heterocyclyl compounds having specific substituents exhibit excellent activity in the inhibition of ACAT, and thus the present invention was accomplished.

CONSTITUTION OF INVENTION

Tricyclic heterocyclyl compounds according to the invention have a general formula I:

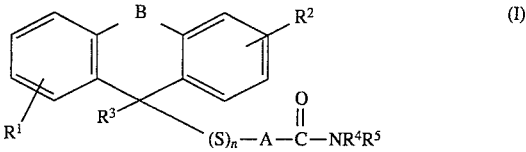

In the above formula, $R^1$ and $R^2$ are the same or different and each represents a hydrogen atom, a lower alkyl group, a lower alkoxy group, a halogen atom or a halogeno-lower alkyl group;

$R^3$ represents a hydrogen atom or a lower alkyl group;

$R^4$ represents a phenyl or naphthyl group, which has 1 to 3 substituents and may optionally be condensed 5- or 6-membered heterocyclyl group (the said substituent represents a lower alkyl, halogeno-lower alkyl, lower alkoxy-(lower alkyl), lower alkylthio(lower alkyl), aralkyl, lower alkenyl, lower alkoxy, aryloxy, aralkyloxy, lower alkylthio, arylthio, aralkylthio, carboxy, lower alkoxycarbonyl, lower alkylsulfinyl, arylsulfinyl, aralkylsulfinyl, lower alkylsulfonyl, arylsulfonyl or aralkylsulfonyl group, a halogen atom, a cyano or nitro group);

$R^5$ represents a hydrogen atom or a lower alkyl group;

A represents a lower alkylene group;

B represents an oxygen or sulfur atom; and n is 0 or 1.

Where $R^1$ and $R^2$ each represents a lower alkyl or halogeno-lower alkyl group; $R^3$ represents a lower alkyl group; a substituent of a phenyl or naphthyl group represented by $R^4$ is a lower alkyl, halogeno-lower alkyl, lower alkoxy(lower alkyl), lower alkylthio(lower alkyl), lower alkylthio, lower alkylsulfinyl or lower alkylsulfonyl group; and $R^5$ represents a lower alkyl group, the term "lower alkyl moiety" is here defined mean a straight or branched $C_1$–$C_6$alkyl group such as, for example, methyl, ethyl, propyl, isopropyl, butyl, isobutyl, pentyl or hexyl, preferably a $C_1$–$C_4$alkyl group, and more preferably a methyl or ethyl group.

Where $R^1$ and $R^2$ each represents a lower alkoxy; and a substituent of a phenyl or naphthyl group represented by $R^4$ is a lower alkoxy, lower alkoxyalkyl or lower alkoxycarbonyl group, the alkyl moiety of the said lower alkoxy group has the same meaning as the lower alkyl group described above.

Where $R^1$ and $R^2$ each represents a halogen atom or a halogeno-lower alkyl group; and a substituent of a phenyl or naphthyl group represented by $R^4$ is a halogen atom or a halogeno-lower alkyl group, the term "halogen" is defined to mean, for example, a fluorine, chlorine, bromine or iodine atom, preferably a fluorine or chlorine atom.

Where $R^4$ represents 5- or 6-membered heterocyclyl group condensed with a phenyl group, it is a heterocyclyl group containing 1 or 2 hetero atoms such as an oxygen, sulfur or nitrogen atom. Examples of such heterocyclyl groups include, for example, furyl, dihydrofuryl, thienyl, dihydrothienyl, thiazolyl, dihydrothiazolyl, pyridyl or tetrahydropyridyl, preferably dihydrofuryl or dihydrothienyl group. The heterocyclyl ring may optionally be substituted and examples of such substituents include a lower alkyl group, preferably a methyl group.

Where a substituent of a phenyl or naphthyl group represented by $R^4$ is an aralkyl, aryloxy, aralkyloxy, arylthio, aralkylthio, arylsulfinyl, aralkylsulfinyl, arylsulfonyl or aralkylsulfonyl group, the term "aryl moiety" is defined to mean a $C_6$–$C_{10}$aryl group such as phenyl, indanyl or naphthyl, preferably a phenyl group. The phenyl ring may optionally be substituted with 1 to 3 substituents (preferably 1); the said substituent represents a lower alkyl (preferably a $C_1$–$C_4$alkyl group) or lower alkoxy group (preferably a $C_1$–$C_4$alkoxy group) or a halogen atom, particularly preferably a methyl, ethyl, methoxy or ethoxy group, a fluorine or chlorine atom.

Where a substituent of a phenyl or naphthyl group represented by $R^4$ is an alkenyl group, it is a $C_2$–$C_6$alkenyl group such as, for example, vinyl, allyl, methallyl, 1-propenyl, 1-butenyl, 2-butenyl, 2-isobutenyl, 1-pentenyl, 2-pentenyl, 1-hexenyl or 2-hexenyl, preferably a $C_2$–$C_4$alkenyl group, more preferably vinyl, allyl or 1-propenyl.

Examples of the said halogeno-lower alkyl group include, for example, fluoromethyl, difluoromethyl, trifluoromethyl, chloromethyl, trichloromethyl, bromomethyl, iodomethyl, 2-fluoroethyl, 2,2,2-trifluoroethyl, 2-chloroethyl, 2-bromoethyl, 3-fluoropropyl, 1-(fluoromethyl)ethyl, 3-chloropropyl, 4-fluorobutyl and 4-chlorobutyl groups, preferably trifluoromethyl and 2,2,2-trifluoroethyl groups.

Examples of the said lower alkoxy(lower alkyl) groups include, for example, methoxymethyl, ethoxymethyl, propoxymethyl, isopropoxymethyl, butoxymethyl, isobutoxymenhyl, 2-methoxyethyl, 2-ethoxyethyl, 3-methoxypropyl, 3-ethoxypropyl, 1-ethoxymethylethyl, 4-ethoxybutyl, propoxymethyl, 2-propoxyethyl, 3-propoxypropyl, 4-propoxybutyl, isopropoxymethyl, 2-isopropoxyethyl, butoxymethyl, 2-butoxyethyl, 3-butoxypropyl and 4-butoxybutyl groups, preferably methoxymethyl, ethoxymethyl, propoxymethyl, butoxymethyl, isobutoxymethyl, 2-methoxyethyl and 3-methoxypropyl groups.

Examples of the said lower alkylthio(lower alkyl) groups include: for example, methylthiomethyl, 2-methylthioethyl, 3-methylthiopropyl, 2-methylthio-1-methylethyl, 4-methylthiobutyl, ethylthiomethyl, 2-ethylthioethyl, 3-ethylthiopropyl, 4-ethylthiobutyl, propylthiomethyl, 2-propylthioethyl, 3-propylthiopropyl, 4-propylthiobutyl, isopropylthiomethyl, 2-isopropylthioethyl, butylthiomethyl, isobutylthiomethyl, 2-butylthioethyl, 3-butylthiopropyl and 4-butylthiobutyl groups, preferably methylthiomethyl, 2-methylthioethyl, ethylthiomethyl, propylthiomethyl, isopropyl thiomethyl, butylthiomethyl and isobutylthiomethyl groups.

Examples of the said aralkyl groups include: a $C_7$–$C_{13}$aralkyl groups such as, for example, benzyl, diphenylmethyl, phenethyl, 3-phenylpropyl, 4-phenylbutyl, naphthylmethyl and 2-naphthylethyl groups, preferably benzyl, phenethyl and 3-phenylpropyl groups.

Examples of the lower alkylene groups represented by A include: a $C_1$–$C_7$alkylene group such as, for example, methylene, 1-methylmethylene, 1,1-dimethylmethylene, ethylene, trimethylene, 1-methylethylene, tetramethylene, pentamethylene, 1-butylmethylene, hexamethylene and heptamethylene groups, preferably a $C_1$–$C_4$alkylene group, more preferably methylene and 1-methylmethylene groups.

$R^4$ represents preferably a phenyl group having 2 or 3 substituents (the said 2 substituents are located in an ortho position with respect to each other) or a phenyl group condensed with an optionally $C_1$–$C_4$alkyl-substituted dihydrofuryl or dihydrothienyl group; more preferably a phenyl group having 2 or 3 substituents (the said 2 substituents are located in an ortho position with respect to each other).

Preferred examples of the substituents involved in $R^4$ include: $C_1$–$C_4$alkyl, halogeno($C_1$–$C_4$alkyl) [particularly trifluoromethyl, 2-fluoroethyl, 3-fluoropropyl and 1-(fluoromethyl)ethyl groups], $C_1$–$C_4$alkoxy($C_1$–$C_4$alkyl), $C_1$–$C_4$alkylthio($C_1$–$C_4$alkyl), benzyl, phenethyl, 3-phenylpropyl, $C_2$–$C_4$alkenyl, $C_1$–$C_4$alkoxy, $C_6$-aryloxy, $C_7$–$C_{10}$aralkyloxy, $C_1$–$C_4$alkylthio, $C_6$–$C_{10}$arylthio, $C_7$–$C_{10}$aralkylthio, $C_1$–$C_4$alkoxycarbonyl, $C_1$–$C_4$alkylsulfinyl and $C_1$–$C_4$alkylsulfonyl groups, a halogen atom and a nitro group; more preferably $C_1$–$C_4$alkyl, $C_1$–$C_4$alkoxy($C_1$–$C_4$alkyl), $C_1$–$C_4$alkylthio($C_1$–$C_4$alkyl), $C_2$–$C_4$alkenyl, $C_1$–$C_4$alkoxy, $C_7$–$C_{10}$aralkyloxy, $C_1$–$C_4$alkylthio, $C_6$-arylthio, benzylthio, phenethylthio, 3-phenylpropylthio, methoxycarbonyl, methylsulfinyl and methanesulfonyl groups, a halogen atom and a nitro group; particularly preferably $C_1$–$C_4$alkyl [particularly methyl, ethyl, propyl and isopropyl groups], $C_1$–$C_4$alkoxy-($C_1$–$C_4$alkyl) [particularly methoxymethyl, methoxyethyl, ethoxymethyl and propoxymethyl group], $C_1$–$C_4$alkylthio($C_1$–$C_4$alkyl) {particularly methylthiomethyl, methylthioethyl, ethylthiomethyl and propiothiomethyl groups}, $C_2$–$C_4$alkenyl {particularly vinyl and allyl groups}, $C_1$–$C_4$alkoxy {particularly methoxy, ethoxy, propoxy and isopropoxy groups}, $C_7$–$C_9$aralkyloxy {particularly benzyloxy and phenethyloxy groups}, $C_1$–$C_4$alkylthio {particularly methylthio, ethylthio, propylthio and isopropylthio groups}, phenyltyhio and $C_7$–$C_9$aralkylthio groups {particularly benzylthio and phenethylthio groups}, a halogen atom {particularly a chlorine atom} and a nitro group; and most preferably ethyl, propyl, isopropyl, methoxymethyl, methylthiomethyl, methoxy, ethoxy, propoxy, isopropoxy, benzyloxy, methylthio, ethylthio, propylthio, isopropylthio and phenylthio groups.

The compounds of formula (I) can exist in the form optical isomers due to the presence of an asymmetric carbon atom. The present invention covers not only mixtures of the isomers but also the individual isomers.

The preferred compounds of general formula (I) are those in which:

(1) $R^1$ and $R^2$ each represents a hydrogen atom, a methyl, ethyl, methoxy or ethoxy group, a fluorine or chlorine atom;

(2) $R^1$ and $R^2$ each represents a hydrogen atom;

(3) $R^3$ represents a hydrogen atom, a methyl or ethyl group;

(4) $R^3$ represents a hydrogen atom or a methyl group;

(5) $R^4$ represents a phenyl group which has 2 or 3 substituents and may optionally be condensed with an optionally $C_1$–$C_4$alkyl-substituted dihydrofuryl or dihydrothienyl ring [the 1 or 2 substituents are located in an ortho position and each is a $C_1$–$C_4$alkyl, halogeno($C_1$–$C_4$alkyl) {particularly a trifluoromethyl, 2-fluoroethyl, 3-fluoropropyl or 1-(fluoromethyl)ethyl group}, $C_1$–$C_4$alkoxy($C_1$–$C_4$alkyl), $C_1$–$C_4$alkylthio($C_1$–$C_4$alkyl), benzyl, phenethyl, 3-phenylpropyl, $C_2$–$C_4$alkenyl, $C_1$–$C_4$alkoxy, $C_6$-aryloxy, $C_7$–$C_{10}$aralkyloxy, $C_1$–$C_4$alkylthio, $C_6$–$C_{10}$arylthio, $C_7$–$C_{10}$aralkylthio, $C_1$–$C_4$alkoxycarbonyl, $C_1$–$C_4$alkylsulfinyl or $C_1$–$C_4$alkylsulfonyl group, a halogen atom, or a nitro group];

(6) $R^4$ represents a phenyl group which has 2 or 3 substituents and may optionally be condensed with an optionally $C_1$–$C_4$alkyl-substituted dihydrofuryl ring [the said 2 substituents are located in an ortho position with respect to each other and each is a $C_1$–$C_4$alkyl, $C_1$–$C_4$alkoxy($C_1$–$C_4$alkyl), $C_1$–$C_4$alkylthio($C_1$–$C_4$alkyl), $C_2$–$C_4$alkenyl, $C_1$–$C_4$alkoxy, $C_7$–$C_{10}$aralkyloxy, $C_1$–$C_4$alkylthio, $C_6$-arylthio, benzylthio, phenethylthio, 3-phenylpropylthio, methoxycarbonyl, methylsulfinyl or methanesulfonyl group, a halogen atom or a nitro group];

(7) $R^4$ represents a phenyl group which has 2 or 3 substituents [2 of the said substituents are located in an ortho position and each is a $C_1$–$C_4$alkyl {particularly a methyl, ethyl, propyl or isopropyl group}, $C_1$–$C_4$alkoxy($C_1$–$C_4$alkyl) {particularly a methoxymethyl, methoxyethyl, ethoxymethyl or ethoxyethyl group}, $C_1$–$C_4$alkylthio($C_1$–$C_4$alkyl) {particularly a methylthiomethyl, methylthioethyl, ethylthiomethyl or ethylthioethyl group}, $C_2$–$C_4$alkenyl {particularly a vinyl or allyl group}, $C_1$–$C_4$alkoxy {particularly a methoxy, ethoxy, propoxy or isopropoxy group}, $C_7$–$C_9$aralkyloxy {particularly a benzyloxy or phenethyloxy group}, $C_1$–$C_4$ alkylthio {particularly a methylthio, ethylthio, propylthio or isopropylthio group}, phenylthio or $C_7$–$C_9$aralkylthio group {particularly a benzylthio or phenethylthio group}, a halogen atom {particularly a chlorine atom) or a nitro group];

(8) $R^5$ represents a hydrogen atom, a methyl or ethyl group;

(9) $R^5$ represents a hydrogen atom;

(10) A represents a $C_1$–$C_4$alkylene group;

(11) A represents a $C_1$–$C_2$alkylene group;

(12) B represents an oxygen atom; and

(13) n is 0.

Examples of the compounds of the said general formula (I) in accordance with the present invention are listed and the compounds of formula (I-1) and formula (I-2) are illustrated in Table 1 and 2, respectively. Such examples are not to be construed as being limitative of the invention.

TABLE 1

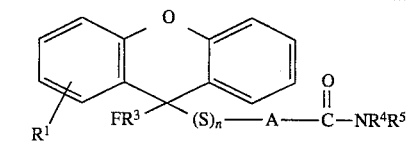 (I-1)

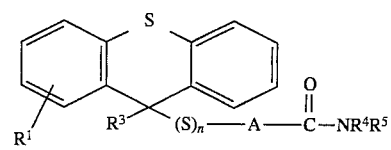 (I-2)

| Cmpd. No. | $R^1$ | $R^3$ | $R^4$ | $R^5$ | A | n |
|---|---|---|---|---|---|---|
| 1-1 | H | H | 2,6-di-iPr—Ph | H | $CH_2$ | 0 |
| 1-2 | H | H | 2,6-di-Et—Ph | H | $CH_2$ | 0 |
| 1-3 | H | H | 2,6-di-Me—Ph | H | $CH_2$ | 0 |
| 1-4 | H | H | 2-Et-6-iPr—Ph | H | $CH_2$ | 0 |
| 1-5 | H | H | 2-Me-6-Pn—Ph | H | $CH_2$ | 0 |
| 1-6 | H | H | 2-Et-6-Pn—Ph | H | $CH_2$ | 0 |
| 1-7 | H | H | 2-Et-6-Bu—Ph | H | $CH_2$ | 0 |
| 1-8 | H | H | 2-Et-6-Pr—Ph | H | $CH_2$ | 0 |
| 1-9 | H | H | 2-Me-6-Pr—Ph | H | $CH_2$ | 0 |
| 1-10 | H | H | 2-Me-6-Bu—Ph | H | $CH_2$ | 0 |
| 1-11 | H | H | 2,6-di-Pr—Ph | H | $CH_2$ | 0 |
| 1-12 | H | H | 2-Et-6-MeSCH$_2$—Ph | H | $CH_2$ | 0 |
| 1-13 | H | H | 2-Et-6-EtSCH$_2$—Ph | H | $CH_2$ | 0 |
| 1-14 | H | H | 2-Me-6-EtSCH$_2$—Ph | H | $CH_2$ | 0 |
| 1-15 | H | H | 2-Me-6-MeSCH$_2$—Ph | H | $CH_2$ | 0 |
| 1-16 | H | H | 2-iPr-6-MeSCH$_2$—Ph | H | $CH_2$ | 0 |
| 1-17 | H | H | 2-iPr-6-EtSCH$_2$—Ph | H | $CH_2$ | 0 |
| 1-18 | H | H | 2-Me-6-MeO—Ph | H | $CH_2$ | 0 |
| 1-19 | H | H | 2-Me-6-BuO—Ph | H | $CH_2$ | 0 |
| 1-20 | H | H | 2-Me-6-EtO—Ph | H | $CH_2$ | 0 |
| 1-21 | H | H | 2-Me-6-PrO—Ph | H | $CH_2$ | 0 |
| 1-22 | H | H | 2-Me-6-iPrO—Ph | H | $CH_2$ | 0 |
| 1-23 | H | H | 2-Et-6-MeO—Ph | H | $CH_2$ | 0 |
| 1-24 | H | H | 2-Et-6-EtO—Ph | H | $CH_2$ | 0 |
| 1-25 | H | H | 2-Et-6-PrO—Ph | H | $CH_2$ | 0 |
| 1-26 | H | H | 2-Et-6-iPrO—Ph | H | $CH_2$ | 0 |
| 1-27 | H | H | 2-Et-6-BuO—Ph | H | $CH_2$ | 0 |
| 1-28 | H | H | 2-Vin-6-MeO—Ph | H | $CH_2$ | 0 |
| 1-29 | H | H | 2-Vin-6-EtO—Ph | H | $CH_2$ | 0 |
| 1-30 | H | H | 2-Vin-6-iPrO—Ph | H | $CH_2$ | 0 |
| 1-31 | H | H | 2-Vin-6-PrO—Ph | H | $CH_2$ | 0 |
| 1-32 | H | H | 2-Vin-6-BuO—Ph | H | $CH_2$ | 0 |
| 1-33 | H | H | 2,4,6-tri-MeO—Ph | H | $CH_2$ | 0 |
| 1-34 | H | H | 2-NO$_2$-6—PhCH$_2$O—Ph | H | $CH_2$ | 0 |
| 1-35 | H | H | 2-NO$_2$-6-Et—Ph | H | $CH_2$ | 0 |
| 1-36 | H | H | 2-NO$_2$-6-Me—Ph | H | $CH_2$ | 0 |
| 1-37 | H | H | 2-Me-6—PhO—Ph | H | $CH_2$ | 0 |
| 1-38 | H | H | 2-Et-6—PhO—Ph | H | $CH_2$ | 0 |
| 1-39 | H | H | 2-iBut-6-iPrO—Ph | H | $CH_2$ | 0 |
| 1-40 | H | H | 2-iBut-6-PrO—Ph | H | $CH_2$ | 0 |
| 1-41 | H | H | 2-iBut-6-Me—Ph | H | $CH_2$ | 0 |

TABLE 1-continued

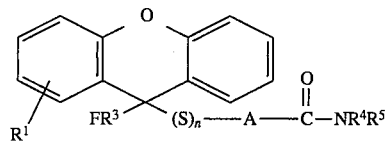

(I-1)

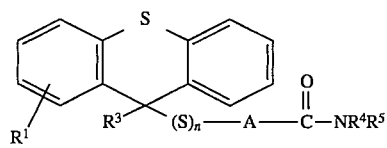

(I-2)

| Cmpd. No. | $R^1$ | $R^3$ | $R^4$ | $R^5$ | A | n |
|---|---|---|---|---|---|---|
| 1-42 | H | H | 2-iBut-6-Et—Ph | H | $CH_2$ | 0 |
| 1-43 | H | H | 2-Vin-6-Me—Ph | H | $CH_2$ | 0 |
| 1-44 | H | H | 2-Vin-6-Et—Ph | H | $CH_2$ | 0 |
| 1-45 | H | H | 2-Cl-6-$CO_2$Me—Ph | H | $CH_2$ | 0 |
| 1-46 | H | H | 2,6-di-Cl—Ph | H | $CH_2$ | 0 |
| 1-47 | H | H | 2-F-6-Cl—Ph | H | $CH_2$ | 0 |
| 1-48 | H | H | 2,6-di-F—Ph | H | $CH_2$ | 0 |
| 1-49 | H | H | 2-F-6-Me—Ph | H | $CH_2$ | 0 |
| 1-50 | H | H | 2-F-6-Et—Ph | H | $CH_2$ | 0 |
| 1-51 | H | H | 2-F-6-iPr—Ph | H | $CH_2$ | 0 |
| 1-52 | H | H | 2-Cl-6-Me—Ph | H | $CH_2$ | 0 |
| 1-53 | H | H | 2-Cl-6-Et—Ph | H | $CH_2$ | 0 |
| 1-54 | H | H | 2-Cl-6-iPr—Ph | H | $CH_2$ | 0 |
| 1-55 | H | H | 2-Cl-6-MeS—Ph | H | $CH_2$ | 0 |
| 1-56 | H | H | 2-Cl-6-EtS—Ph | H | $CH_2$ | 0 |
| 1-57 | H | H | 2-Cl-6-iPrS—Ph | H | $CH_2$ | 0 |
| 1-58 | H | H | 2-Cl-6-PrS—Ph | H | $CH_2$ | 0 |
| 1-59 | H | H | 2-Cl-6-iPnS—Ph | H | $CH_2$ | 0 |
| 1-60 | H | H | 2-Cl-6-BuS—Ph | H | $CH_2$ | 0 |
| 1-61 | H | H | 2-Cl-6—PhS—Ph | H | $CH_2$ | 0 |
| 1-62 | H | H | 2-Cl-6-(p-TolS)—Ph | H | $CH_2$ | 0 |
| I-63 | H | H | 2-Cl-6-(p-MeOPhS)—Ph | H | $CH_2$ | 0 |
| 1-64 | H | H | 2-Cl-6-(o-ClPhS)—Ph | H | $CH_2$ | 0 |
| 1-65 | H | H | 2-F-6-MeS—Ph | H | $CH_2$ | 0 |
| 1-66 | H | H | 2-F-6-EtS—Ph | H | $CH_2$ | 0 |
| 1-67 | H | H | 2-F-6-iPrS—Ph | H | $CH_2$ | 0 |
| 1-68 | H | H | 2-F-6-PrS—Ph | H | $CH_2$ | 0 |
| 1-69 | H | H | 2-F-6-BuS—Ph | H | $CH_2$ | 0 |
| 1-70 | H | H | 2-F-6-iPnS—Ph | H | $CH_2$ | 0 |
| 1-71 | H | H | 2-F-6—$PhCH_2S$—Ph | H | $CH_2$ | 0 |
| 1-72 | H | H | 2-F-6—$PhCH_2CH_2S$—Ph | H | $CH_2$ | 0 |
| 1-73 | H | H | 2-Cl-6—$PhCH_2S$—Ph | H | $CH_2$ | 0 |
| 1-74 | H | H | 2-Cl-6—$PhCH_2CH_2S$—Ph | H | $CH_2$ | 0 |
| 1-75 | H | H | 2-Cl-6-MeO—Ph | H | $CH_2$ | 0 |
| 1-76 | H | H | 2-Cl-6-EtO—Ph | H | $CH_2$ | 0 |
| 1-77 | H | H | 2-Cl-6-iPrO—Ph | H | $CH_2$ | 0 |
| 1-78 | H | H | 2-Cl-6-PrO—Ph | H | $CH_2$ | 0 |
| 1-79 | H | H | 2-F-6-MeO—Ph | H | $CH_2$ | 0 |
| 1-80 | H | H | 2-F-6-EtO—Ph | H | $CH_2$ | 0 |
| 1-81 | H | H | 2-F-6-iPrO—Ph | H | $CH_2$ | 0 |
| 1-82 | H | H | 2-F-6-PrO—Ph | H | $CH_2$ | 0 |
| 1-83 | H | H | 2-F-6—$PhCH_2O$—Ph | H | $CH_2$ | 0 |
| 1-84 | H | H | 2-Cl-6—$PhCH_2O$—Ph | H | $CH_2$ | 0 |
| 1-85 | H | H | 2-F-6—PhO—Ph | H | $CH_2$ | 0 |
| 1-86 | H | H | 2-Cl-6—PhO—Ph | H | $CH_2$ | 0 |
| 1-87 | H | H | 2-Me-6—PhO—Ph | H | $CH_2$ | 0 |
| 1-88 | H | H | 2-Et-6—PhO—Ph | H | $CH_2$ | 0 |
| 1-89 | H | H | 2-Me-6—$PhCH_2O$—Ph | H | $CH_2$ | 0 |
| 1-90 | H | H | 2-Et-6—$PhCH_2O$—Ph | H | $CH_2$ | 0 |
| 1-91 | H | H | 2-Pr-6—$PhCH_2O$—Ph | H | $CH_2$ | 0 |
| 1-92 | H | H | 2-iPr-6—$PhCH_2O$—Ph | H | $CH_2$ | 0 |
| 1-93 | H | H | 2-MeO-6—$PhCH_2O$—Ph | H | $CH_2$ | 0 |
| 1-94 | H | H | 2-EtO-6—$PhCH_2O$—Ph | H | $CH_2$ | 0 |
| 1-95 | H | H | 2,6-di-iPrO—Ph | H | $CH_2$ | 0 |
| 1-96 | H | H | 2,6-di-EtO—Ph | H | $CH_2$ | 0 |
| 1-97 | H | H | 2,6-di-MeO—Ph | H | $CH_2$ | 0 |
| 1-98 | H | H | 2,6-di-iPr—Ph | H | CH(Me) | 0 |
| 1-99 | H | H | 2,6-di-Et—Ph | H | CH(Me) | 0 |
| 1-100 | H | H | 2-Et-6-MeO—Ph | H | CH(Me) | 0 |
| 1-101 | H | H | 2-Et-6-EtO—Ph | H | CH(Me) | 0 |
| 1-102 | H | H | 2-Et-6-iPrO—Ph | H | CH(Me) | 0 |
| 1-103 | H | H | 2-Et-6—PhO—Ph | H | CH(Me) | 0 |

TABLE 1-continued

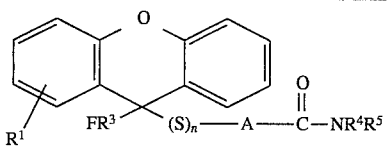

(I-1)

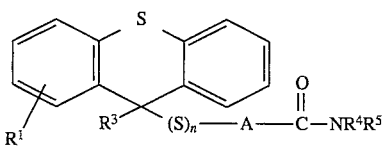

(I-2)

| Cmpd. No. | R¹ | R³ | R⁴ | R⁵ | A | n |
|---|---|---|---|---|---|---|
| 1-104 | H | H | 2-Et-6—PhCH₂O—Ph | H | CH(Me) | 0 |
| 1-105 | H | H | 2-Et-6-MeS—Ph | H | CH(Me) | 0 |
| 1-106 | H | H | 2-Et-6-EtS—Ph | H | CH(Me) | 0 |
| 1-107 | H | H | 2-Et-6-iPrS—Ph | H | CH(Me) | 0 |
| 1-108 | H | H | 2-Et-6-PrS—Ph | H | CH(Me) | 0 |
| 1-109 | H | H | 2-Et-6—PhS—Ph | H | CH(Me) | 0 |
| 1-110 | H | H | 2-Et-6—PhCH₂S—Ph | H | CH(Me) | 0 |
| 1-111 | H | H | 2-Me-6-iPrS—Ph | H | CH(Me) | 0 |
| 1-112 | H | H | 2-Me-6-EtS—Ph | H | CH(Me) | 0 |
| 1-113 | H | H | 2-Me-6-MeS—Ph | H | CH(Me) | 0 |
| 1-114 | H | Me | 2,6-di-iPr—Ph | H | CH₂ | 0 |
| 1-115 | H | Me | 2,6-di-Et—Ph | H | CH₂ | 0 |
| 1-116 | H | Me | 2-Et-6-MeO—Ph | H | CH₂ | 0 |
| 1-117 | H | Me | 2-Et-6-EtO—Ph | H | CH₂ | 0 |
| 1-118 | H | Me | 2-Et-6-iPrO—Ph | H | CH₂ | 0 |
| 1-119 | H | Me | 2-Et-6—PhO—Ph | H | CH₂ | 0 |
| 1-120 | H | Me | 2-Et-6—PhCH₂O—Ph | H | CH₂ | 0 |
| 1-121 | H | Me | 2-Et-6-MeS—Ph | H | CH₂ | 0 |
| 1-122 | H | Me | 2-Et-6-EtS—Ph | H | CH₂ | 0 |
| 1-123 | H | Me | 2-Et-6-iPrS—Ph | H | CH₂ | 0 |
| 1-124 | H | Me | 2-Et-6-PrS—Ph | H | CH₂ | 0 |
| 1-125 | H | Me | 2-Et-6—PhS—Ph | H | CH₂ | 0 |
| 1-126 | H | Me | 2-Et-6—PhCH₂S—Ph | H | CH₂ | 0 |
| 1-127 | H | Me | 2-Et-6-MeSO₂—Ph | H | CH₂ | 0 |
| 1-128 | H | Me | 2-Et-6-EtSO₂—Ph | H | CH₂ | 0 |
| 1-129 | H | Me | 2-Et-6-iPrSO₂—Ph | H | CH₂ | 0 |
| 1-130 | H | Me | 2-Et-6-PrSO₂—Ph | H | CH₂ | 0 |
| 1-131 | H | Me | 2-Et-6—PhCH₂SO₂—Ph | H | CH₂ | 0 |
| 1-132 | H | Me | 2-Me-6-Et—Ph | H | CH₂ | 0 |
| 1-133 | H | H | 2-Et-6-MeSO₂—Ph | H | CH(Me) | 0 |
| 1-134 | H | H | 2-Et-6-EtSO₂—Ph | H | CH(Me) | 0 |
| 1-135 | H | H | 2-Et-6-iPrSO₂—Ph | H | CH(Me) | 0 |
| 1-136 | H | H | 2-Cl-6-MeSO₂—Ph | H | CH(Me) | 0 |
| 1-137 | H | H | 2-Cl-6-MeS—Ph | H | CH(Me) | 0 |
| 1-138 | H | H | 2-F-6-MeS—Ph | H | CH(Me) | 0 |
| 1-139 | H | H | 2-F-6-MeSO₂—Ph | H | CH(Me) | 0 |
| 1-140 | H | H | 2-F-6-MeSO₂—Ph | H | CH(Et) | 0 |
| 1-141 | H | H | 2-F-6-MeS—Ph | H | CH(Et) | 0 |
| 1-142 | H | H | 2-F-6-EtS—Ph | H | CH(Et) | 0 |
| 1-143 | H | H | 2-F-6-iPrS—Ph | H | CH(Et) | 0 |
| 1-144 | H | Me | 2,6-di-iPr—Ph | H | CH(Me) | 0 |
| 1-145 | H | Me | 2,6-di-Et—Ph | H | CH(Me) | 0 |
| 1-146 | H | Me | 2-Et-6-MeS—Ph | H | CH(Me) | 0 |
| 1-147 | H | Me | 2-Et-6-MeSO₂—Ph | H | CH(Me) | 0 |
| 1-148 | H | Me | 2-Et-6-MeO—Ph | H | CH(Me) | 0 |
| 1-149 | H | Me | 2-Et-6-EtO—Ph | H | CH(Me) | 0 |
| 1-150 | H | Me | 2-Et-6-iPrO—Ph | H | CH(Me) | 0 |
| 1-151 | H | Me | 2-Et-6—PhCH₂O—Ph | H | CH(Me) | 0 |
| 1-152 | H | Me | 2-Et-6-EtS—Ph | H | CH(Me) | 0 |
| 1-153 | H | Me | 2-Et-6-EtSO₂—Ph | H | CH(Me) | 0 |
| 1-154 | H | Me | 2-Et-6-iPrS—Ph | H | CH(Me) | 0 |
| 1-155 | H | Bu | 2,6-di-iPr—Ph | H | CH₂ | 0 |
| 1-156 | H | Bu | 2,6-di-Et—Ph | H | CH₂ | 0 |
| 1-157 | H | Bu | 2-Et-6-MeS—Ph | H | CH₂ | 0 |
| 1-158 | H | Bu | 2-Et-6-MeSO₂—Ph | H | CH₂ | 0 |
| 1-159 | H | Pr | 2,6-di-Et—Ph | H | CH₂ | 0 |
| 1-160 | H | Pr | 2,6-di-iPr—Ph | H | CH₂ | 0 |
| 1-161 | H | Pr | 2-Et-6-MeS—Ph | H | CH₂ | 0 |
| 1-162 | H | Me | 2,6-di-iPr—Ph | H | C(Me)₂ | 0 |
| 1-163 | H | Me | 2,6-di-Et—Ph | H | C(Me)₂ | 0 |
| 1-164 | H | H | 2,6-di-iPr—Ph | H | CH₂ | 1 |
| 1-165 | H | H | 2,6-di-Et—Ph | H | CH₂ | 1 |

TABLE 1-continued (I-1)

(I-2)

| Cmpd. No. | R¹ | R³ | R⁴ | R⁵ | A | n |
|---|---|---|---|---|---|---|
| 1-166 | H | H | 2-Et-6-MeS—Ph | H | $CH_2$ | 1 |
| 1-167 | H | H | 2-Et-6-MeSO₂—Ph | H | $CH_2$ | 1 |
| 1-168 | H | H | 2-Et-6-iPrO—Ph | H | $CH_2$ | 1 |
| 1-169 | H | Me | 2,6-di-iPr—Ph | H | $CH_2$ | 1 |
| 1-170 | H | Me | 2,6-di-Et—Ph | H | $CH_2$ | 1 |
| 1-171 | H | Me | 2-Et-6-MeS—Ph | H | $CH_2$ | 1 |
| 1-172 | H | H | 2-Et-6-MeS—Ph | H | $CH_2$ | 0 |
| 1-173 | H | H | 2-iPr-6-MeS—Ph | H | $CH_2$ | 0 |
| 1-174 | H | H | 2-Pr-6-MeS—Ph | H | $CH_2$ | 0 |
| 1-175 | H | H | 2-Bu-6-MeS—Ph | H | $CH_2$ | 0 |
| 1-176 | H | H | 2-iPn-6-MeS—Ph | H | $CH_2$ | 0 |
| 1-177 | H | H | 2-Et-6-MeSO₂—Ph | H | $CH_2$ | 0 |
| 1-178 | H | H | 2-Et-6-MeSO—Ph | H | $CH_2$ | 0 |
| 1-179 | H | H | 2-iPr-6-EtS—Ph | H | $CH_2$ | 0 |
| 1-180 | H | H | 2-iPr-6-EtSO₂—Ph | H | $CH_2$ | 0 |
| 1-181 | H | H | 2-Et-6-EtS—Ph | H | $CH_2$ | 0 |
| 1-182 | H | H | 2-Et-6-EtSO₂—Ph | H | $CH_2$ | 0 |
| 1-183 | H | H | 2-Me-6-EtSO₂—Ph | H | $CH_2$ | 0 |
| 1-184 | H | H | 2-Me-6-EtSO—Ph | H | $CH_2$ | 0 |
| 1-185 | H | H | 2-Et-6—PhCH₂S—Ph | H | $CH_2$ | 0 |
| 1-186 | H | H | 2-Et-6—PhCH₂SO₂—Ph | H | $CH_2$ | 0 |
| 1-187 | H | H | 2-Et-6—PhS—Ph | H | $CH_2$ | 0 |
| 1-188 | H | H | 2-Et-6—PhSO₂—Ph | H | $CH_2$ | 0 |
| 1-189 | H | H | 2-Et-6—PhCH₂CH₂S—Ph | H | $CH_2$ | 0 |
| 1-190 | H | H | 2-Et-6—PhCH₂CH₂SO₂—Ph | H | CH | 0 |
| 1-191 | H | H | 2-Me-6—PhCH₂S—Ph | H | $CH_2$ | 0 |
| 1-192 | H | H | 2-Me-6—PhCH₂SO₂—Ph | H | $CH_2$ | 0 |
| 1-193 | H | H | 2-MeOCH₂-6-MeS—Ph | H | $CH_2$ | 0 |
| 1-194 | H | H | 2-MeOCH₂-6-MeSO₂—Ph | H | $CH_2$ | 0 |
| 1-195 | H | H | 2-MeOCH₂-6-EtS—Ph | H | $CH_2$ | 0 |
| 1-196 | H | H | 2-MeOCH₂-6-EtSO₂—Ph | H | $CH_2$ | 0 |
| 1-197 | H | H | 2-MeOCH₂-6-iPrSO₂—Ph | H | $CH_2$ | 0 |
| 1-198 | H | H | 2-MeOCH₂-6-iPrS—Ph | H | $CH_2$ | 0 |
| 1-199 | H | H | 2-MeOCH₂-6—PhS—Ph | H | $CH_2$ | 0 |
| 1-200 | H | H | 2-MeOCH₂-6—PhSO₂—Ph | H | $CH_2$ | 0 |
| 1-201 | H | H | 2-EtOCH₂-6-MeS—Ph | H | $CH_2$ | 0 |
| 1-202 | H | H | 2-EtOCH₂-6-MeSO₂—Ph | H | $CH_2$ | 0 |
| 1-203 | H | H | 2-EtOCH₂-6-EtS—Ph | H | $CH_2$ | 0 |
| 1-204 | 1-MeO | H | 2,6-di-iPr—Ph | H | $CH_2$ | 0 |
| 1-205 | 2-MeO | H | 2,6-di-iPr—Ph | H | $CH_2$ | 0 |
| 1-206 | 3-MeO | H | 2,6-di-iPr—Ph | H | $CH_2$ | 0 |
| 1-207 | 4-MeO | H | 2,6-di-iPr—Ph | H | $CH_2$ | 0 |
| 1-208 | 1-MeO | H | 2-Et-6-MeS—Ph | H | $CH_2$ | 0 |
| 1-209 | 2-MeO | H | 2-Et-6-MeS—Ph | H | $CH_2$ | 0 |
| 1-210 | 3-MeO | H | 2-Et-6-MeS—Ph | H | $CH_2$ | 0 |
| 1-211 | 4-MeO | H | 2-Et-6-MeS—Ph | H | $CH_2$ | 0 |
| 1-212 | 2-MeO | H | 2-Et-6-MeO—Ph | H | $CH_2$ | 0 |
| 1-213 | 2-MeO | H | 2-Et-6-EtS—Ph | H | $CH_2$ | 0 |
| 1-214 | 2-MeO | H | 2-Et-6-iPrS—Ph | H | $CH_2$ | 0 |
| 1-215 | H | H | 2-EtOCH₂-6-EtSO₂—Ph | H | $CH_2$ | 0 |
| 1-216 | H | H | 2-EtOCH₂-6—PhS—Ph | H | $CH_2$ | 0 |
| 1-217 | H | H | 2-EtOCH₂-6—PhSO₂—Ph | H | $CH_2$ | 0 |
| 1-218 | H | H | 2-MeOCH₂-6—PhCH₂S—Ph | H | $CH_2$ | 0 |
| 1-219 | H | H | 2-MeOCH₂-6—PhCH₂SO₂—Ph | H | $CH_2$ | 0 |
| 1-220 | H | Me | 2-MeOCH₂-6-MeS—Ph | H | $CH_2$ | 0 |
| 1-221 | H | Me | 2-MeOCH₂-6-EtS—Ph | H | $CH_2$ | 0 |
| 1-222 | H | Me | 2-MeOCH₂-6-MeSO₂—Ph | H | $CH_2$ | 0 |
| 1-223 | H | H | 2,6-di-MeS—Ph | H | $CH_2$ | 0 |
| 1-224 | H | H | 2,6-di-EtS—Ph | H | $CH_2$ | 0 |
| 1-225 | H | H | 2,6-di-MeSO₂—Ph | H | $CH_2$ | 0 |
| 1-226 | H | H | 2,6-di-Me-Bezf | H | $CH_2$ | 0 |
| 1-227 | H | H | 2,2,6-tri-Me-Bezf | H | $CH_2$ | 0 |

TABLE 1-continued (I-1)

Structure showing two phenyl rings connected through a carbon bearing R³ and linked via O bridge, with substituent R¹ and chain (S)ₙ—A—C(=O)—NR⁴R⁵

(I-2)

Structure showing two phenyl rings connected through a carbon bearing R³ and linked via S bridge, with substituent R¹ and chain (S)ₙ—A—C(=O)—NR⁴R⁵

| Cmpd. No. | $R^1$ | $R^3$ | $R^4$ | $R^5$ | A | n |
|---|---|---|---|---|---|---|
| 1-228 | H | Me | 2,6-di-Me-Bezf | H | $CH_2$ | 0 |
| 1-229 | H | H | 2-Me-6-Et-Bezf | H | $CH_2$ | 0 |
| 1-230 | H | H | 2,2-di-Me-6-Et-Bezf | H | $CH_2$ | 0 |
| 1-231 | H | Me | 2-Me-6-Et-Bezf | H | $CH_2$ | 0 |
| 1-232 | H | Me | 2,2-di-Me-6-Et-Bezf | H | $CH_2$ | 0 |
| 1-233 | H | H | 2,2-di-Me-6-Et-Bezf | H | $CH_2$ | 1 |
| 1-234 | H | H | 2-Cl-6-$CH_2$OMe—Ph | H | $CH_2$ | 0 |
| 1-235 | H | H | 2-Cl-6-$CH_2$OPr—Ph | H | $CH_2$ | 0 |
| 1-236 | H | H | 2-Cl-6-$CH_2$OEt—Ph | H | $CH_2$ | 0 |
| 1-237 | H | H | 2-Cl-6-$CH_2$OBu—Ph | H | $CH_2$ | 0 |
| 1-238 | H | H | 2-Cl-6-$CH_2$OPn—Ph | H | $CH_2$ | 0 |

TABLE 2

| Cmpd. No. | $R^1$ | $R^3$ | $R^4$ | $R^5$ | A | n |
|---|---|---|---|---|---|---|
| 2-1 | 3-Cl | H | 2,6-di-iPr—Ph | H | $CH_2$ | 0 |
| 2-2 | 3-Cl | H | 2,6-di-Et—Ph | H | $CH_2$ | 0 |
| 2-3 | H | H | 2,6-di-iPr—Ph | H | $CH_2$ | 0 |
| 2-4 | H | H | 2,6-di-Et—Ph | H | $CH_2$ | 0 |
| 2-5 | H | H | 2-Et-6-MeS—Ph | H | $CH_2$ | 0 |
| 2-6 | H | H | 2-Et-6-iPrO—Ph | H | $CH_2$ | 0 |
| 2-7 | H | H | 2,6-di-Me—Bezf | H | $CH_2$ | 0 |
| 2-8 | H | H | 2-Me-6-Et—Bezf | H | $CH_2$ | 0 |
| 2-9 | H | H | 2,2-di-Me-6-Et—Bezf | H | $CH_2$ | 0 |
| 2-10 | H | Me | 2,6-di-iPr—Ph | H | $CH_2$ | 0 |
| 2-11 | H | Me | 2,6-di-Et—Ph | H | $CH_2$ | 0 |
| 2-12 | H | H | 2-Cl-6-MeO$CH_2$—Ph | H | $CH_2$ | 0 |
| 2-13 | H | H | 2-Cl-6-EtO$CH_2$—Ph | H | $CH_2$ | 0 |
| 2-14 | H | H | 2-SMe-6-MeO$CH_2$—Ph | H | $CH_2$ | 0 |

In the above Tables 1 and 2 the abbreviations used have the following significance.

Bezf: 2,3-dihydrobenzo[b]furan-7-yl

Bu: butyl

But: butenyl

Et: ethyl

Me: methyl

Ph: phenyl

Pn: pentyl

Pr: propyl

Tol: tolyl

Vin: vinyl

The compounds in accordance with the present invention can easily be prepared by the following method.

Method A

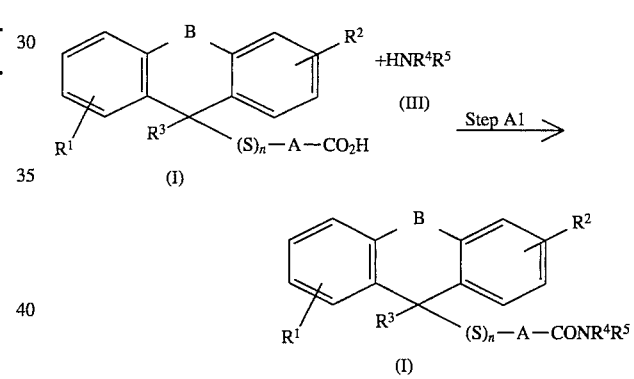

In the above formulae, $R^1$, $R^2$, $R^3$, $R^4$, $R^5$, A, B and n are as defined above.

Method A involves a method for preparing a compound of formula (I) of the invention.

Step A1 involves the preparation of a compound of formula (I) and can be accomplished by reacting a carboxylic acid compound having a general formula (II) or its reactive derivative with an amine compound having a general formula (III). The step is carried out by using a method such as an acid halide, mixed acid anhydride, activated ester and condensation reaction methods.

Using an acid halide method, the desired compound of a formula (I) can be prepared by reacting a carboxylic acid having a formula (II) with a halogenating agent to form an acid halide and then reacting with a compound of formula (III) in an inert solvent in the presence or absence of a base.

Examples of the acid-halogenating agents used include, for example, thionyl chloride, oxalyl chloride, phosphorus pentachloride and thionyl bromide, preferably chloride and oxalyl chloride.

Examples of the bases used include, for example, organic amines such as triethylamine, N-Methylmorpholine, pyridine, 4-dimethylaminopyridine, 2,6-lutidine and N,N-dimethylaniline; alkaline metal bicarbonates such as sodium bicarbonate or potassium bicarbonate; and alkaline metal carbonates such as sodium carbonate or potassium carbonate; preferably organic amines.

There is no particular limitation upon the nature of the solvent used, provided that it has no adverse effect upon the reaction. Examples of such solvents include: for example, hydrocarbons such as hexane, cyclohexane, benzene, toluene or xylene; halogenated hydrocarbons such as dichloromethane, 1,2-dichloroethane or carbon tetrachloride; ethers such as ether, tetrahydrofuran or dioxane; ketones such as acetone; amides such as N,N-dimethylformamide, N,N-dimethylacetamide, N-methyl-2-pyrrolidone or hexamethylphosphoramide; sulfoxides such as dimethyl sulfoxide; preferably hydrocarbons, halogenated hydrocarbons, ethers and amides; and particularly preferably halogenated hydrocarbons.

The reaction temperature depends upon the starting compounds of formula (II) and (III), the nature of the solvent used and the like, but both reactions of a compound (II) with a halogenating agent and those of the resulting acid halide with a compound (III) are usually carried out at a temperature of −20° C. to 100° C. Preferably the reaction of a compound (II) with a halogenating agent is carried out at a temperature of 0° C. to 30° C. and the reaction of the resulting acid halide with a compound (III) at a temperature of 0° C. to 50° C. Although the time required for the reaction depends upon the reaction temperature and the like, both reactions complete within a period of 30 minutes to 24 hours. Preferably the first reaction takes from 1 to 10 hours and the subsequent reaction takes from 1 to 20 hours.

Using a mixed acid anhydride method, the desired compound (I) can be prepared by reacting a compound (II) with lower alkyl halogenoformate or di(lower alkyl) cyanophosphate to form a mixed acid anhydride and then reacting with a compound (III).

The reaction for preparing a mixed acid anhydride is preferably carried out by reacting a compound (II) with lower alkyl halogenoformate such as ethyl chloroformate or isobutyl chloroformate of di(lower alkyl) cyanophosphate such as diethyl cyanophosphate in an inert solvent in the presence of a base.

The bases and inert solvents to be used are the same as used in the above acid halide method.

Although the reaction temperature depends upon the starting compound (II), the nature of the solvent and the like, the reaction is usually carried out at a temperature of −20° C. to 50° C. (preferably 0° C. to 30° C.). The time required for the reaction depends upon the reaction temperature and the like, but the reaction complete generally within a period of 1 to 24 hours.

The reaction of a mixed acid anhydride with a compound (III) is preferably carried out in an inert solvent in the presence or absence of a base. The bases and inert solvent to be used are the same as used in the above acid halide method.

Although the reaction temperature depends upon the starting compound (III), the nature of the solvent and the like, the reaction is usually carried out at a temperature of −20° C. to 100° C. (preferably 0° C. to room temperature). The time required for the reaction depends upon the reaction temperature and the like, but the reaction completes generally within a period of 1 to 24 hours.

Using a activated ester method, the desired compound (I) can be prepared by reacting a compound (II) with an agent for producing activated ester (for example, N-hydroxy compounds such as N-hydroxysuccinimide or N-hydroxybenzotriazole) in the presence of a condensing agent (for example, dicyclohexylcarbodiimide or carbonyldiimidazole) to form an activated ester and then reacting with a compound (III).

The reaction for preparing an activated ester is preferably carried out in an inert solvent and the solvents to be used are the same as used in the above acid halide method.

Although the reaction temperature depends upon the starting compounds of formulae (II) and (III), the nature of the solvent and the like, the reaction for preparing an activated ester is usually carried out at a temperature of −20° C. to 50° C. (preferably −10° C. to 30° C.) and the reaction of a compound (III) with an activated ester at a temperature of −20° C. to 50° C. (preferably 0° C. to 30° C.). The time required for the reaction depends upon the reaction temperature and the like, but both reaction complete generally within a period of 1 to 24 hours.

Using a condensation reaction method, the desired compound of formula (I) can be prepared by reacting directly a compound (II) with a compound (III) in the presence of a condensing agent [for example, dicyclohexylcarbodiimide, carbonyldiimidazole, 1-(N,N-dimethylaminopropyl)-3-ethylcarbodiimide hydrochloride]. This reaction is carried out in a similar manner to the above reaction for preparing an activated ester.

After completion of the reaction, each of the desired compounds can be recovered from the reaction mixture by conventional means. For example, one such technique comprises: collecting precipitated crystals by filtration; or adding water; extracting with water-immiscible organic solvent such as ethyl acetate; drying the organic extract; and distilling off the solvent to leave the desired product behind as a residue. If necessary, the compound produced can be purified by conventional means, for example, recrystallization, column chromatography or the like.

The compound (I), in which the substituent involved in the definition of R is a lower alkenyl, can be catalytically reduced to a compound in which the said substituent involved in the definition of $R^4$ is the corresponding alkyl group.

The catalytic reduction is carried out by contacting the corresponding alkenyl compound with hydrogen in an inert solvent in the presence of a catalyst.

Examples of the catalysts used include: for example, palladium on charcoal, platinum oxide, rhodium on alumina and ruthenium on charcoal, preferably palladium on charcoal.

The hydrogen pressure used is, for example, ordinary pressure to 5 atmospheric pressure, preferably ordinary pressure.

There is no particular limitation upon the nature of the solvent used, provided that it has no adverse effect upon the reaction. Examples of the solvents used include: for example, alcohols such as methanol or ethanol; ehters such as tetrahydrofuran or dioxane; and esters such as ethyl acetate; preferably ethers.

The reaction is usually carried out at a temperature of from 0° C. to 100° C. (preferably room temperature to 50° C.). The time required for the reaction depends upon the reaction temperature and the like, but the reaction completes within a period of 30 minutes to 24 hours (preferably 1 to 10 hours).

After completion of the reaction, each of the desired compounds can be recovered from the reaction mixture by conventional means. For example, one such method comprises: diluting the reaction mixture with an inert solvent such as dichloromethane; removing off the catalyst used by filtration by the aid of Celite; and distilling off the solvent from the filtrate to leave the desired product behind as a residue. Each of the compounds produced can be further purified, if necessary, by such conventional techniques as recrystallization or column chromatography.

The compound (I), in which the substituent involved in the definition of $R^4$ is an alkylthio or arylthio group, can be oxidized to give a compound in which the substituent involved in the definition of $R^4$ is the corresponding sulfenyl or sulfonyl group.

Oxidation is carried out by contacting the corresponding alkylthio, arylthio or aralkylthio compound with an oxidizing agent in an inert solvent in the presence of a catalyst.

Examples of the oxidizing agents used include: for example, peroxides such as m-chloroperbenzoic acid, perbenzoic acid, peracetic acid, hydrogen peroxide or tert-butyl hydroperoxide, preferably m-chloroperbenzoic acid and tert-butyl hydroperoxide.

Examples of the catalysts used include: transition metal acetylacetonate such as vanadium acetylacetonate or molybdenum acetylacetonate, preferably vanadium acetylacetonate.

There is no particular limitation upon the nature of the solvent used, provided that it has no adverse effect upon the reaction. Examples of the solvents used include: for example, alcohols such as methanol or ethanol; and halogenated hydrocarbons such as dichloromethane, chloroform or 1,2-dichloroethane; preferably halogenated hydrocarbons.

In order to remove acidic materials from the peroxide used, this reaction can also be carried out in the presence of alkaline metal carbonates such as sodium carbonate or potassium carbonate or an aqueous solution thereof.

In this reaction, there can mainly be obtained the corresponding sulfenyl compound by using 1 to 1.5 moles of an oxidizing agent per mole of the compound (I) and there can mainly be obtained the corresponding sulfonyl compound by using 2 to 3 moles of an oxidizing agent per mole of the compound (I).

The reaction is usually carried out at a temperature of −10° C. to 80° C. (preferably 0° C. to 30° C.). Although the time required for the reaction depends upon the reaction temperature and the like, the reaction completes within a period of 30 minutes to 10 hours preferably 1 to 5 hours).

After completion of the reaction, the desired compound of this reaction can be recovered from the reaction mixture by conventional means. For example, the reaction mixture is freed from insoluble materials, if any, by filtration and the solvent is distilled off from the filtrate to leave the desired product behind as a residue. Alternatively, the residue thus obtained is mixed with water and a water-immiscible organic solvent, after which the extract is dried and the solvent is evaporated off to give the desired compound. The compound produced can be further purified, if necessary, by such conventional techniques as recrystallization or column chromatography.

The starting compounds (II) used in Method A are either known or can easily be prepared in a manner known per se, for example in analogy to the procedure described in Yakugaku Zasshi, 77, 1145(1957) and J. Org. Chem., 21, 186(1956).

Some of the compounds (II) can alternatively be prepared by the following methods.

Method B

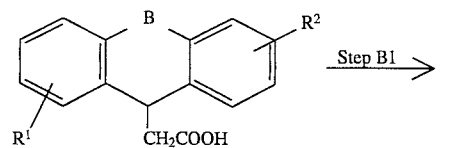

(II a)

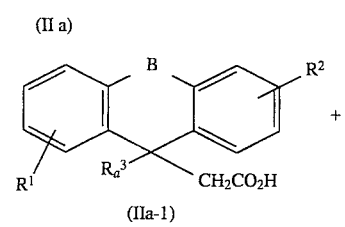

(IIa-1)

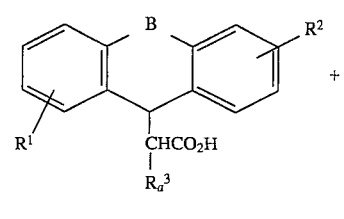

(IIa-2)

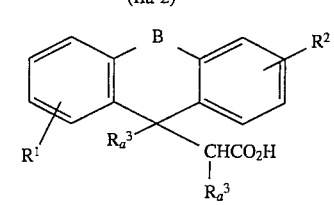

(IIa-3)

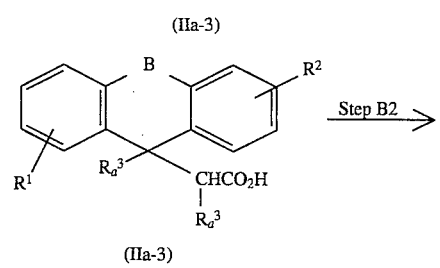

(IIa-3)

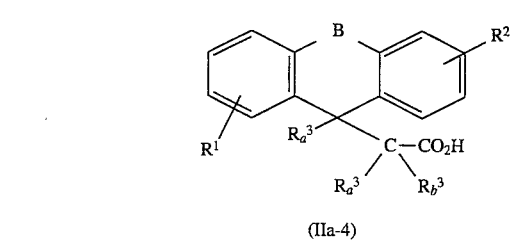

(IIa-4)

In the formulae given above, $R^1$, $R^2$ and B are as defined above; and $R_a^3$ and $R_b^3$ are the same or different and each has the same meaning as defined for $R^3$ excepting a hydrogen atom, provided that the carbon numbers of $R_a^3$ and $R_b^3$ in total are not more than 6.

Method B involves the preparation of a compound ($II_a$-1), that is, a compound (II) in which $R^3$ represents a lower alkyl, A represents a methylene group, and n is 0; a compound ($II_a$-2), that in which $R^3$ represents a hydrogen atom, A represents a formula: —CH($R_a^3$)— (wherein $R_a^3$ is as defined above), and n is 0; a compound ($II_a$-3), that in which $R^3$ represents a lower alkyl group A represents a formula: —CH($R_a^3$)— (wherein $R_a^3$ is as defined above) and n is 0; and a compound ($II_a$-4), that in which $R^3$ represents a lower alkyl group A represents a formula: —C($R_a^3$)($R_a^3$)— (wherein $R_a^3$ and $R_b^3$ are as defined above), and n is 0.

Step B1 consists of the preparation of compounds of formulae ($II_a$-1), ($II_a$-2) and ($II_a$-3) by reacting a compound having a general formula ($II_a$) with a base (for example, alkaline metal hydrides such as lithium hydride or sodium hydride) in an inert solvent (for example, ethers such as ether or tetrahydrofuran) at a temperature of from room temperature to 100° C. (preferably 0° to 30° C.) for a period of from 10 minutes to 3 hours (preferably 15 minutes to 1 hour) to form an alkaline metal salt of a carboxylic acid; reacting with a base [for example, metal amides such as lithium isopropylamide, lithium bis(trimethylsilyl)amide or sodium bis(trimethylsilyl)amide] at a temperature of from −60° C. to 50° C. (preferably −30° C. to room temperature) for a period of from 5 minutes to 2 hours (preferably 10 minutes to 1 hour) to produce a carbanion; and finally reacting the carbonion with a compound of a general formula: $R_a^3$—X (IV) [where $R_a^3$ is as defined above and X represents a halogen atom (preferably a chlorine, bromine or iodine atom)] at a temperature of from −50° C. to 100° C. (preferably −50° C. to room temperature) for a period of from 15 minutes to 5 hours (preferably 30 minutes to 3 hours).

Step B2 consists of the preparation of a compound ($II_a$-4) by using as a starting compound a compound ($II_a$) and a compound of general formula: $R_b^3$—X ($IV_a$) (wherein $R_b^3$ and X are as defined above) instead of a compound (IV). The reaction is carried out in a similar manner as Step B1 given above.

The starting compounds (III) used in Method A are either known or can easily be produced according to method known per se.

Some of the compound (III) can alternatively be produced according to the following methods.

Method C

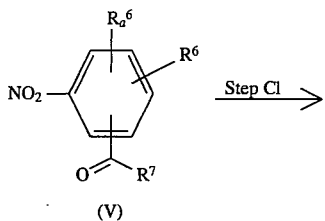

(V)

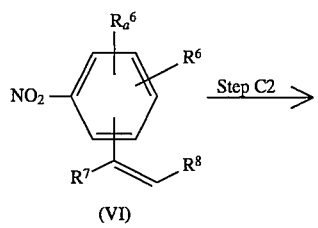

(VI)

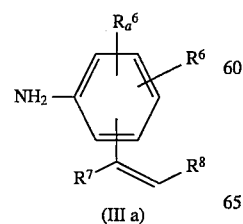

(III a)

Method D

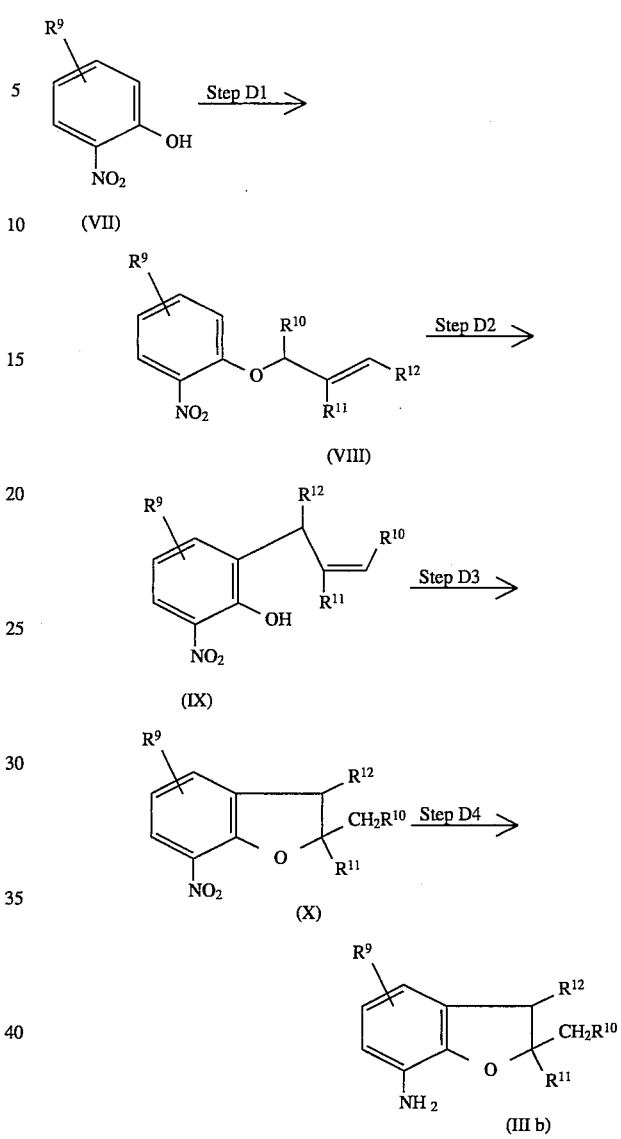

In the formulae given above, $R^6$ and $R_a^6$ are the same or different and each has the same meaning as $R^4$ excepting a lower alkenyl and nitro groups of the phenyl substituents involved in the definition of $R^4$; $R^7$ and $R^8$ are the same or different and each represents a hydrogen atom or a lower alkyl group (provided that the carbon number of a group having a formula: —C($R^7$)=$CHR^8$ in total is from 2 to 6); $R^9$, $R^{11}$ and $R^{12}$ are the same or different and each represents a hydrogen atom or a lower alkyl group; and $R^{10}$ represents a hydrogen atom or a $C_1$–$C_5$alkyl group.

Method C involves the preparation of a compound ($III_a$), that is, a compound (III) in which $R^4$ represents a formula:

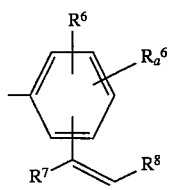

(in the formula $R^6$, $R_a^6$, $R^7$ and $R^8$ are as defined above) and $R^5$ represents a hydrogen atom.

Step C₁ consists of the preparation of a compound of a general formula (VI) by reacting a compound (V) with a compound having general formula:

(in the formula, $R^8$ is as defined above and $R^{13}$ represents a $C_6$–$C_{10}$aryl group such as a phenyl or naphthyl group) at a temperature of from 0° to 50° C. (preferably about room temperature) for a period of from 30 minutes to 24 hours (preferably 1 to 20 hours).

The compound (XI) can be prepared by reacting a compound of a general formula:

with a base (for example, alkyl alkaline metals such as methyllithium, butyllithium or phenyllithium) in an inert solvent (for example, ethers such as ether or tetrahydrofuran) at a temperature of −20° C. to 50° C. (preferably about room temperature) for a period of from 30 minutes to 10 hours (preferably 1 to 5 hours).

Step C₂ involves the preparation of a compound (III$_a$) by reacting a compound (VI) with a reducing agent (for example, zinc, iron, aluminium etc.) in an inert solvent (for example, alcohols such as methanol or ethanol, or aqueous alcohols such as methanol or ethanol, or aqueous alcohol) in the presence of an acid (for example, hydrochloric acid, acetic acid etc.) or a base (for example, sodium hydroxide, potassium hydroxide etc.) at a temperature of from room temperature to 200° C. (preferably 50° C. to 150° C.) for a period of from 30 minutes to 10 hours (preferably 1 to 5 hours). The compound (III$_a$) can also be prepared from a compound (VI) by catalytic reduction and the reaction is carried out in a similar manner as the corresponding reaction of the said Method A.

Method D involves the preparation of a compound of formula (III$_b$), that is, a compound (III) in which $R^4$ represents a formula:

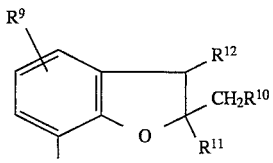

(in the formula, $R^9$, $R^{10}$, $R^{11}$ and $R^{12}$ are as defined above) and $R^5$ represents a hydrogen atom.

Step D1 consists of the preparation of a compound of a general formula (VIII) by reacting a compound having a general formula (VII) with a compound of a general formula:

(in the formula, $R^{10}$, $R^{11}$, $R^{12}$ and X are as defined above) in an inert solvent (for example, ketones such as acetone or methyl ethyl ketone) in the presence of a base (for example, alkaline metal carbonates such as sodium carbonate or potassium carbonate) at a temperature of from 0° to 200° C. (preferably room temperature to 100° C.) for a period of from 30 minutes to 5 hours (preferably 1 to 3 hours). Preferably the reaction is carried out in the presence of a small amount of alkaline metal iodides such as sodium iodide or potassium iodide.

Step D2 consists of the preparation of a compound of a general formula (IX) by subjecting a compound (IX) to Clasisen rearrangement in an inert solvent (for example, diphenyl ether, N,N-dimethylaniline etc.) upon heating at a temperature of from 50° C. to 250° C. (preferably 100° C. to 200° C.) for a period of from 30 minutes to 15 hours (preferably 1 to 10 hours).

Step D3 consists of the preparation of a compound of a general formula (X) by reacting a compound (IX) with an acid (for example, Lewis acids such as boron trifluoride, boron trifluoride etherate or magnesium chloride, proton acids such as 47% hydrobromic acid-acetic acid etc.) in an inert solvent (for example, halogenated hydrocarbons such as dichloromethane or chloroform) at a temperature of from 0° to 50° C. (preferably about room temperature) for a period of from 30 minutes to 10 hours (preferably 1 to 5 hours).

Step D4 consists of the preparation of a compound (III$_b$) by reducing a compound (X) in a similar manner as the said Step B1 of Method B.

In each of these steps, the desired compound can be recovered from the reaction mixture according to conventional means. An example of one such technique comprises: filtering the reaction mixture if insoluble materials exist; neutralizing properly if the reaction mixture is acidic or basic; distilling off the solvent; adding water to the residue thus obtained; extracting with a water-immiscible organic solvent; drying the organic extract; and finally distilling off the solvent. If necessary, the products can be further purified by conventional means, for example, recrystallization, column chromatography or the like.

Effect of the Invention

As can be seen from the following Test Example, the compounds (I) of the invention have an excellent ACAT inhibiting activity and show a low toxicity. Accordingly, they are useful for the treatment and prophylaxis of atherosclerosis.

TEST EXAMPLE 1

ACAT Inhibiting Effect

ACAT inhibiting activities were determined according to the improved test method in vitro reported by Ross et al. [A. C. Ross etal., J. Biol. Chem., 259, 815–819(1984)].

According to the procedure described in A. C. Ross et al., J. Biol. Chem., 257, 2453–2459(1982), rat liver microsome was prepared from a rat of Sprague-Dawley strain fasted overnight to make an enzyme fraction. To a 0.15M potassium phosphate buffer solution (pH 7.4) containing 100 μM of [14C]oleoyl-CoA, 2 mM of dithiothreitol and 80 μM of bovine serum albumin were added 60–100 μg of the microsome fraction, and a 5 μl solution of a test compound in dimethylsulfoxide (2.5% v/v) was added to the above phosphate buffer solution to make 200 μl. The mixture was warmed at 37° C. for 4 minutes and then the enzyme reaction was stopped by adding 1 ml of ethanol under stirring. To the reaction mixture were added 2 ml of hexane. After stirring, 1 ml of a hexane solution was taken out and the solvent was evaporated in a stream of nitrogen. Cholesteryl oleate resulted from the enzyme reaction was separated by thin layer chromatography through silica gel using a 85:15:1 mixture of hexane, diethyl ether and acetic acid as a developing solvent. An ACAT activity was determined by measuring radioactivity and a inhibiting rate (%) was calculated by comparing a control activity with that of the test compound at given concentrations.

Compounds of Examples 1, 2, 3, 9, 10, 11, 16, 18-B and 25 were evaluated as having an excellent inhibiting activity.

For the treatment or prophylaxis of atherosclerosis the compounds (I) are administered alone or as a pharmaceutical composition in admixture with one or more carriers, excipients and/or diluents. They can be administered orally in the form of powders, granules, tablets, capsules etc. or parenterally by injection etc. The dose varies depending upon the condition of the patient and upon the route and type of administration but, in general, the compounds of the invention can be administered orally at one-time dose of from 1 to 2000 mg, particularly 5 to 300 mg, or intravenously at one-time dose of from about 0.1 to 100 mg, particularly 0.5 to 50 mg once to thrice a day.

The present invention is explained in detail by the following Examples and Referential Examples. Such examples are not to be construed as being limitative of the invention.

EXAMPLES

Example 1

N-[2,6-Bis (1-methylethyl)phenyl]-2-(9H-xanthen-9-yl)acetamide

To a solution of 51 mg (0.21 mmol) of 2-(9H-xanthen-9yl)acetic acid in 2 ml of dichloromethane were added 0.1 ml (1.1 mmol) of oxalyl chloride and one drop of N,N-dimethylformamide with ice-cooling, and the resulting mixture was stirred for 3 hours and freed from the solvent and an excess of the reagent by distillation under reduced pressure. The residue was again dissolved in 2 ml of dichloromethane, and 93 mg (0.53 mmol) of 2,6-bis(1-methylethyl)aniline and 0.2 ml of pyridine were added thereto with ice-cooling, followed by stirring at room temperature for 5 hours. After distilling off the solvent, the residue thus obtained was purified by column chromatography through 15 g of silica gel using a 30:0–1 mixture of dichloromethane and ethyl acetate as an eluent to give 78 mg (92%) of the desired compound as crystals.

m.p. 231°–232.5° C. (recrystallized from ethyl acetate).

IR spectrum (KBr) cm$^{-1}$: 3253, 1651, 1517, 1481, 1457, 1259, 757.

NMR spectrum (CDCl$_3$) ppm: 1.05 (6H, d, J=7 Hz), 2.27 (2H, septet, J=7 Hz), 2.78 (2H, d, J=7 Hz), 4.73 (1H, t, J=7 Hz), 6.3–6.5 (1H, br.s), 6.8–7.5 (11H, m).

Example 2

N-(2,6-Diethylphenyl)-2-(9H-xanthen-9-yl)acetamide

Following the procedure of Example 1, but using 2,6-diethylanililne instead of 2,6-bis(1-methylethyl)aniline, there was obtained the title compound in 83% yield.

m.p. 228.5°–229.5° C.

IR spectrum (KBr) cm$^{-}$: 1646, 1523, 1481, 1261, 753.

Example 3

N- (2-Ethyl-6-methylthiomethylphenyl)-2- (9H-xanthen-9-yl)acetamide

Following the procedure of Example 1, but using 2-ethyl-6-methylthiomethylaniline instead of 2,6-bis(1-methylethyl)aniline, there was obtained the title compound in 62% yield.

m.p. 122°–123° C.

IR spectrum (KBr) cm$^{-1}$: 1648, 1514, 1480, 1458, 1258.

Example 4

N-(2-Butoxy-6-vinylphenyl)-2- (9H-xanthen-9-yl)acetamide

Following the procedure of Example 1, but using 2-butoxy-6-vinylaniline instead of 2,6-bis(1-methylethyl)aniline, there was obtained the title compound in 64% yield.

m.p. 176°–177° C.

IR spectrum (KBr) cm$^{-1}$: 1655, 1533, 1481, 1260, 754.

Example 5

N-(2-Methoxy- 6-vinylphenyl)-2-(9H-xanthen-9-yl)acetamide

Following the procedure of Example 1, but using 2-methoxy-6-vinylaniline (a compound of Referential Example 1) instead of 2,6-bis(1-methylethyl)aniline, there was obtained the title compound in 28% yield.

m.p. 230.5°–231° C.

IR spectrum (KBr) cm$^{-1}$: 1653, 1528, 1482, 1262, 754.

Example 6

N(2-Isopropoxy-6-vinylphenyl)-2-(9H-xanthen-9-yl)acetamide

Following the procedure of Example 1, but using 2-isopropoxy-6-vinylaniline instead of 2,6-bis(1-methylethyl)aniline, there was obtained the title compound in 63% yield.

m.p. 171.5°–172° C.

IR spectrum (KBr) cm$^{-1}$: 1654, 1530, 1481, 1260, 752.

Example 7

N-(2,4,6-Trimethoxyphenyl)-2-(9H -xanthen-9-yl)acetamide

Following the procedure of Example 1, but using 2,4,6-trimethoxyaniline instead of 2,6-bis(1-methylethyl)aniline, there was obtained the title compound in 82% yield.

m.p. 223°–224° C.

IR spectrum (KBr) cm$^{-1}$: 1655, 1537, 1261, 1136, 755.

Example 8

N-(2-Benzyloxy-6-nitrophenyl)-2- (9H-xanthen-9-yl)acetamide

Following the procedure of Example 1, but using 2-benzyloxy-6-nitroaniline instead of 2,6-bis(1-methylethyl)aniline, there was obtained the title compound in 14% yield.

m.p. 200°–200.5° C.

IR spectrum (KBr) cm$^{-1}$: 1669, 1550, 1514, 1362, 1261.

Example 9

N-(2-Ethyl-6-methylthiophenyl)-2-(9H-xanthen-9-yl)acetamide

Following the procedure of Example 1, but using 2-ethyl-6-methylthioaniline instead of 2,6-bis(1-methylethyl)aniline, there was obtained the title compound in 63% yield.

m.p. 139°–140° C.

IR spectrum (KBr) cm$^{-1}$: 1649, 1516, 1481, 1457, 1258.

Example 10

N-(2-Ethyl-6-isopropylthiophenyl)-2-(9H-xanthen-9-yl)acetamide

Following the procedure of Example 1, but using 2-ethyl-6-isopropylaniline instead of 2,6-bis(1-methylethyl)aniline, there was obtained the title compound in 89% yield.

m.p. 184.5°–186° C.

IR spectrum (Nujol) cm$^{-1}$: 1648, 1518, 1482, 1260, 760.

Example 11

N-(2-Ethyl-6-phenylthiophenyl)-2-(9H-xanthen-9-yl)acetamide

Following the procedure of Example 1, but using 2-ethyl-6-phenylthiophenylaniline instead of 2,6-bis(1-methylethyl)aniline, there was obtained the title compound in 69% yield.

m.p. 237°–239° C.

IR spectrum (Nujol) cm$^{-1}$: 1648, 1518, 1482, 1260, 760.

Example 12

N-(2-Methylthio-6-methoxymethylphenyl)-2-(9H-xanthen-9-yl)acetamide

Following the procedure of Example 1, but using 2-methylthio-6-methoxymethylaniline instead of 2,6-bis(1-methylethyl)aniline, there was obtained the title compound in 40% yield.

m.p. 231°–232° C.

IR spectrum (KBr) cm$^{-1}$: 1649, 1519, 1481, 1261, 1114, 758.

Example 13

N-(2-Chloro-6-methoxycarbonylphenyl)-2-(9H-xanthen-9-yl)acetamide

Following the procedure of Example 1, but using 2-chloro-6-methoxycarbonylaniline instead of 2,6-bis(1-methylethyl)aniline, there was obtained the title compound in 26% yield.

m.p. 178°–179° C.

IR spectrum (KBr) cm$^{-1}$: 1729, 1665, 1516, 1481, 1292, 761.

Example 14

N-(6-Ethyl-2,3-dihydro-2-methylbenzo[b]furan-7-yl)-2-(9H-xanthen-9-yl)acetamide

Following the procedure of Example 1, but using 7-amino-6-ethyl-2,3-dihydro-2-methylbenzo[b]furan (a compound of Referential Example 2) instead of 2,6-bis(1-methylethyl)aniline, there was obtained the title compound in 62% yield.

m.p. 278°–279° C.

IR spectrum (Nujol) cm$^{-1}$: 1653, 1540, 1378, 1262, 765.

Example 15

N-(6-Methyl-2,3-dihydro-2-methylbenzo[b]furan-7-yl)-2-(9H-xanthen-9-yl)acetamide Following the procedure of Example 1, but using 7-amino-6-methyl-2,3-dihydro-2-methylbenzo[b]furan instead of 2,6-bis(1-methylethyl)aniline, there was obtained the title compound in 74% yield.

m.p. 290°–291° C.

IR spectrum (Nujol) cm$^{-1}$: 1650, 1538, 1378, 1262, 760.

Example 16

N-[2,6-Bis(1-methylethyl)phenyl]-2-(9H-xanthen-9-yl)propanamide

Following the procedure of Example 1, but using 2-(9H-xanthen-9-yl)propionic acid instead of 2-(9H-xanthen-9-yl)acetic acid, there was obtained the title compound in 67% yield.

m.p. 209.5°–211° C.

IR spectrum (KBr) cm$^{-1}$: 1644, 1516, 1456, 1257, 757.

Example 17

N-[2,6-Bis(1-methylethyl)phenyl]-2-(9H-xanthen-9yl)hexanamide

Following the procedure of Example 1, but using 2-(9H-xanthen-9-yl)hexanoic acid instead of 2-(9H-xanthen-9-yl)acetic acid, there was obtained the title compound in 22% yield.

m.p. 188°–189° C.

IR spectrum (KBr) cm$^{-1}$: 1655, 1504, 1475, 1250, 751.

Example 18

N-[2,6-Bis(1-methylethyl)phenyl]-2-(9-methyl-9H-xanthen-9-yl)propanamide
(Compound A) and
N-[2,6-bis(1-methylethyl)phenyl]-2-(9-methyl-9H-xanthen-9-yl)acetamide
(Compound B)

Following the procedure of Example 1, but using a mixture of 2-(9-methyl-9H-xanthen-9-yl)propionic acid, 2-(9-methyl-9H-xanthen-9-yl)acetic acid and 2-(9H-xanthen-9-yl)propionic acid prepared in Referential Example 3 instead of 2-(9H-xanthen-9-yl)acetic acid, there was obtained the title compound after purifying by column chromatography through silica gel using a 1:8 mixture of ethyl acetate and hexane, and dichloromethane as an eluent.

Compound A

Yield: 32%.

m.p. 140°–141° C.

IR spectrum (KBr) cm$^{-1}$: 1659, 1501, 1474, 1456, 1246.

Compound B

Yield: 37%.

m.p. 151°–152° C.

IR spectrum (KBr) cm$^{-1}$: 1653, 1512, 1484, 1455, 1438, 1265.

In this reaction, there was also obtained a compound of Example 16 in 10% yield.

Example 19

N-(2,6-Dimethylphenyl)-2-(9H-xanthen-9-yl)acetamide

Following the procedure of Example 1, but using 2,6-dimethylaniline instead of 2,6-bis(1-methylethyl)aniline, there was obtained the title compound in 75% yield.

m.p. 249°–250° C.

IR spectrum (KBr) cm$^{-1}$: 1648, 1526, 1481, 1263, 755.

Example 20

N-[2,6-Bis(1-methylethyl)phenyl]-2-methyl-2-(9-methyl-9H-xanthen- 9-yl)propanamide Following the procedure of Example 1, but using 2-methyl-2-(9-methyl-9H-xanthen-9-yl)propanoic acid instead of 2-(9H-xanthen-9-yl)acetic acid to form the corresponding acid chloride and reacting the acid chloride with 2,6-bis(1-methylethyl)aniline in 1,2-dichloroethane for 16 hours in the presence of N,N-dimethyl-4-aminopyridine (an equivalent) and pyridine (10 equivalents) under refluxing followed by working-up in a similar manner as Example 1, there was obtained the title compound in 45% yield.

m.p. 182°–183° C.

IR spectrum (KBr) cm$^{-1}$: 1644, 1491, 1471, 1442, 1243.

Example 21

N-[2,6-Bis(1-methylethyl)phenyl]-2-[(9H-xanthen-9-yl)thio] acetamide

Following the procedure of Example 1, but using 2-[(9H-xanthen-9-yl)thio]acetic acid instead of 2-(9H-xanthen-9-yl)acetic acid, there was obtained the title compound in 51% yield.

m.p. 213°–214. 5° C.

IR spectrum (Nujol) cm$^{-1}$: 1655, 1518, 1380, 1258, 760.

Example 22

N-[2,6-Bis(1-methylethyl)phenyl]-2-(2-chloro-9H-thioxanthen- 9-yl)]acetamide

Following the procedure of Example 1, but using 2-[(9H-thioxanthen-9-yl)thio]acetic acid instead of 2-(9H-xanthen-9-yl)acetic acid, there was obtained title compound in 81% yield.

m.p. 224°–225° C.

IR spectrum (KBr) cm$^{-1}$: 1650, 1531, 1464, 737.

Example 23

N-(2- Ethyl -6-methoxyphenyl)-2-(9H-xanthen-9-yl)acetamide

A solution of 258 mg (0.62 mmol) of N-(2-methoxy-6-vinylphenyl)-2-(9H-xanthen-9-yl)acetamide in 54 ml of tetrahydrofuran was vigorously stirred at room temperature for 10 hours in the presence of 20 mg of 10% palladium on charcoal in a stream of hydrogen. The reaction mixture was filtered with the aid of Celite and the catalyst was washed with tetrahydrofuran. The filtrate and the washings were combined and concentrated. The residue was recrystallized from a mixture of dichloromethane and hexane to give 99 mg (57%) of the title compound as crystals.

m.p. 238°–239° C.

IR spectrum (KBr) cm$^{-1}$: 1652, 1528, 1482, 1261, 754.

NMR spectrum (CDCl$_3$) δ ppm:

0.89 (2/3H,t, J=7.5 Hz), 1.11 (7/3H, t, J=7.5 Hz), 2.12 (4/9H, br.), 2.31 (4/9H, br.d, J=7 Hz), 2.46 (14/9H, q, J=7.5 Hz), 2.75 (14/9H, d, J=7 Hz), 3.55 (2/3H, s), 3.68 (7/3H, s), 4.72 (1H, t J=7 Hz), 6.38 (2/9H, s), 6.46 (7/9H, s), 6.63 (2/9H, d, J=8 Hz), 6.70 (7/9H, d, J=8 Hz), 6.85 (7/9H, d, J=8 Hz), 6.99–7.37 (51/7H, m), 7.39 (2H, d, J=6 Hz).

Example 24

N-(2-Ethyl-6-butoxyphenyl)-2-9H-xanthen-9-yl)acetamide

Following the procedure of Example 23, but using N-(2-butoxy-6-vinylphenyl)-2-(9H-xanthen-9-yl)acetamide instead of N-(2-methoxy-6-vinylphenyl)-2-(9H-xanthen-9-yl)acetamide, there was obtained the title compound in 92% yield.

m.p. 195°–196° C.

IR spectrum (KBr) cm$^{-1}$: 1650, 1529, 1481, 1461, 753.

Example 25

N-(2-Ethyl -6-isopropoxyphenyl)-2-(9H-xanthen-9-yl)acetamide

Following the procedure of Example 23, but using N-(2-isoporpoxy- 6-vinylphenyl)-2-(9H-xanthen-9-yl)acetamide instead of N-(2-methoxy-6-vinylphenyl)-2-(9H-xanthen-9-yl)acetamide, there was obtained the title compound in 57% yield.

m.p. 185–186° C.

IR spectrum (KBr) cm$^{-1}$: 1653, 1528, 1480, 1260, 754.

Example 26

N-(2-Ethyl -6-methylsulfonylphenyl)-2-(9H-xanthen-9-yl)acetamide (Compound A) and N-(2-ethyl-6-methylsulfinylphenyl)- 2-(9H -xanthen-9-yl)acetamide (Compound B)

To a suspension of 100 mg (0.26 mmol) of N-(2-ethyl-6-methylthiophenyl)- 2-(9H-xanthen-9-yl)acetamide in 3 ml of dichloromethane were added 0.56 ml of a 1N aqueous solution of sodium hydrogencarbonate and then 95 mg (0.39 mmol) of 70% m-chloroperbenzoic acid with ice-cooling, and the resulting mixture was stirred at the same temperature for 40 minutes. The reaction mixture was diluted with ether and the ethereal layer was washed with water followed by distilling off the solvent. The residue was purified by column chromatography through 10 g of silica gel using a 12:1 mixture of dichloromethane and ethyl acetate as an eluent to give 68 mg (63%) of a methylsulfonyl derivative (Compound A). The column was further eluted with a 1:2 mixture of dichloromethane and ethyl acetate to give 25 mg (24%) of a methylsulfinyl derivative (Compound B).

Compound A m.p. 195°–196° C. (recrystallized from a mixture of dichloromethane and hexane).

IR spectrum (KBr) $cm^{-1}$: 1650, 1535, 1481, 1457, 1314, 1261.

NMR spectrum ($CDCl_3$) δ ppm: 1.18 (3H, t, J=7.5 Hz), 2.53 (2H, q, J=7.5 Hz), 2.55 (3H, s), 2.85 (2H, d, J=7 Hz), 4.71 (1H, t, J=7 Hz), 7.05 (2H, t, J=8 Hz), 7.15 (2H, d, J=8 Hz), 7.24 (2H, t, J=8 Hz), 7.38 (2H, d, J=8 Hz), 7.39 (1H, t, J=8 Hz), 7.59 (1H, d, J=8 Hz), 7.80 (1H, d, J=8 Hz).

Compound B

IR spectrum ($CHCl_3$) $cm^{-1}$: 1665, 1515, 1480, 1458, 1255, 1028.

NMR spectrum ($CDCl_3$) δ ppm: 1.05 (3H, t, J=7.5 Hz), 2.32 (2H, q, J=7.5 Hz), 2.57 (3H, s), 2.75 (1H, dd, J=7.5, 15 Hz), 2.80 (1H, dd, J=6.5, 15 Hz), 4.65 (1H, dd, J=6.5, 7.5 Hz), 7.02–7.14 (4H, m), 7.20–7.38 (6H, m), 7.48–7.52 (1H, m), 8.09 (1H, m, br.s).

Example 27

N-(2–Chloro-6-methoxymethylphenyl)-2-(9H-xanthen-9-yl)acetamide

Following the procedure of Example 1, but using 2-chloro-6-methoxymethylaniline instead of 2,6-bis(1-methylethyl)aniline, there was obtained the title compound in 49% yield.

m.p. 184°–185° C.

IR spectrum (KBr) $cm^{-1}$: 1651, 1522, 1480, 1455, 757.

Reference Example 1

2-Methoxy-6-vinylaniline a) 2-Methoxy-6-vinyl-1-nitrobenzene

A suspension of 4.35 g (12.2 mmol) of triphenylmethylphosphonium bromide in 30 ml of tetrahydrofuran was cooled to −10° C. and 12.1 mmol of a 1.44M solution of butyllithium were dropwise added thereto over a period of 5 minutes. After the resulting mixture was stirred at 0° C. for 40 minutes, a solution of 1.99 g (11.0 mmol) of 3-methoxy-2-nitrobenzaldehyde in 10 ml of tetrahydrofuran was dropwise added thereto over a period of 10 minutes. The temperature of the reaction mixture was allowed to rise to room temperature. After stirring for 16 hours, the reaction mixture was poured into an aqueous solution of ammonium chloride followed by extracting with ether. The ethereal extract was washed with a saturated aqueous solution of sodium chloride and the solvent was distilled off. The residue was purified by column chromatography through 100 g of silica gel using a 15–20:100 mixture of ethyl acetate and hexane as an eluent to give 1.50 g (76%) of the title compound.

m.p. 55°–56° C. (recrystallized from a mixture of ethyl acetate and hexane).

IR spectrum (Nujol) $cm^{-1}$: 1576, 1528, 1373, 1280, 1065.

NMR spectrum ($CDCl_3$) δ ppm: 3.86 (3H, s), 5.45 (1H, dd, J=2, 11 Hz), 5.80 (1H, dd, J=2, 18 Hz), 6.66 (1H, dd, J=11, 18 Hz), 6.88–7.55 (3H, m).

b) 2-Methoxy-6-vinylaniline

A mixture of 500 mg (2.8 mmol) of the compound prepared in Referential Example 1(a), 0.46 ml of a 20% aqueous solution of sodium hydroxide and 7 ml of ethanol was heated under refluxing for an hour and a half. The reaction mixture was filtered by the aid of Celite and insoluble materials were washed with ethanol. The filtrate and the washings were combined and the solvent was distilled off. The residue was partitioned between a 2:1 mixture of ethyl acetate and hexane, and water. The organic layer was washed with water and the solvent was distilled off. The residue was purified by column chromatography through 8 g of silica gel using a 1:1 mixture of dichloromethane and hexane as an eluent to give 366 mg (88%) of the title compound as an oil.

NMR spectrum ($CDCl_3$) δ ppm: 3.6–4.3 (2H, br.s), 3.84 (3H, s), 5.1–5.3 (1H, m), 5.3–5.6 (1H, m), 5.7–5.8 (1H, m), 6.5–7.1 (3H, m).

Reference Example 2

7-Amino-6-ethyl-2,3-dihydro-2-methylbenzo[b]furan a) 2-Allyloxy-6-ethyl-1-nitrobenzene A mixture consisted of 3.15 g (18.2 mmol) of 2-ethyl-6-hydroxy-1-nitrobenzene, 4.44 g (36.7 mmol) of allyl bromide, 2.70 g (19.5 mmol) of potassium carbonate, 262 mg (1.75 mmol) of sodium iodide and 30 ml of acetone was heated under refluxing for 2 hours. After cooling, the reaction mixture was diluted with ether and the diluted mixture was filtered to remove inorganic substances. The filtrate was concentrated and the concentrate was purified by column chromatography through 150 g of silica gel using a 1:9 mixture of ether and hexane as an eluent to give 3.68 g (98%) of the title compound as an oil.

IR spectrum (Liq) $cm^{-1}$: 1612, 1582, 1530, 1372, 1280.

NMR spectrum ($CDCl_3$) ppm: 1.21 (3H, t, J=7 Hz), 2.59 (2H, q, J=7 Hz), 4.52–4.65 (2H, m), 5.13–5.58 (2H, m), 5.72–6.34 (1H, m), 6.78–6.96 (2H, m), 7.21–7.49 (1H, m).

b) 3-Allyl-6-ethyl-2-hydroxy-1-nitrobenzene

A solution of 807 mg (3.88 mmol) of the compound prepared in Referential Example 2(a) in 2 ml of diphenyl ether was heated at 180° C. for 5 hours. The reaction mixture was cooled and diluted with ether. The diluted mixture was extracted with a 2N aqueous solution of sodium hydroxide and the aqueous extract was acidified by 2N hydrochloric acid followed by extracting with ether. The ethereal extract was washed with a saturate aqueous solution of sodium chloride and the solvent was distilled off. The residue was purified by column chromatography through 25 g of silica gel using a 5:95 mixture of ether and hexane as an eluent to give 583 mg (73%) of the title compound as an oil.

IR spectrum (Liq) $cm^{-1}$: 3350, 1640, 1607, 1588, 1543, 1420.

NMR spectrum ($CDCl_3$) δ ppm: 1.22 (3H, t, J=7 Hz), 2.89 (2H, q, J=7 Hz), 3.42 (2H, d, J=6 Hz), 4.90–5.32 (2H, m), 5.68–6.36 (1H, m), 6.80 (1H, d, J=8 Hz), 7.31 (1H, d, J=8 Hz), 10.31 (1H, s).

c)
7-Amino-6-ethyl-2,3-dihydro-2-methylbenzo[b]furan

To a solution of 581 mg (2.80 mmol) of the compound prepared in Referential example 2(b) in 6 ml of dichloromethane was dropwise added 0.70 ml (5.6 mmol) of boron trifluoride etherate with ice-cooling, and the resulting mixture was stirred at room temperature for 3 hours. The reaction was stopped by adding a saturated aqueous solution of sodium hydrogencarbonate and the reaction mixture was extracted with ether. The ethereal extract was subsequently washed with a 2N aqueous solution of sodium hydroxide, water and a saturated aqueous solution of sodium chloride and the solvent was distilled off. The residue (202 mg) containing a ring-closed compound was dissolved in methanol and the solution was vigorously stirred at room temperature for 50 minutes in a stream of hydrogen in the presence of 27 mg of 10% palladium on charcoal. The reaction mixture was filtered by the aid of Celite and the catalyst was washed methanol. The filtrate and the washings were combined and the solvent was distilled off. The residue was purified by column chromatography through 20 g of silica gel using a 1:4 mixture of ether and hexane as an eluent to give 129 mg (26%) of the title compound as an oil.

IR spectrum (Liq) cm$^{-1}$: 3470, 3380, 1635, 1608, 1495, 928.

NMR spectrum (CDCl$_3$) δ ppm: 1.22 (3H, t, J=7 Hz), 1.45 (3H, d, J=6 Hz), 2.48 (2H, q, J=7 Hz), 2.75 (1H, dd, J=8, 15 Hz), 3.25 (1H, dd, J=8, 15 Hz), 2.9–4.0 (2H, br.s), 4.90 (1H, tq, J=8, 6 Hz), 6.59 (2H, s).

Reference Example 3

2-(9-Methyl-9H-xanthen-9-yl)propionic acid (Compound A),

2-(9-methyl-9H-xanthen-9-yl)acetic acid (Compound B) and

2-(9H-xanthen-9-yl)propionic acid (Compound C)

To a suspension of 55 mg (1.26 mmol) of sodium hydride previously washed with n-hexane in 5 ml of tetrahydrofuran were added 316 mg (3.13 mmol) of diisopropylamine, and then a solution of 300 mg (1.25 mmol) of 2-(9H-xanthen-9-yl)acetic acid in 4 ml of tetrahydrofuran was dropwise added thereto. After completion of the addition, the resulting mixture was heated under refluxing for 20 minutes and then cooled to −15° C., after which 1.2 ml (1.9 mmol) of a 1.6M n-butyllithium solution were added thereto followed by stirring at the same temperature for 15 minutes. To the mixture was dropwise added a solution of 531 mg of methyl iodide in 2 ml of tetrahydrofuran over a period of 10 minutes, after which stirring was continued at the same temperature for an hour. With ice-cooling the reaction was stopped by addition of a diluted aqueous solution of sodium hydrogencarbonate and the reaction mixture was washed with dichloromethane. The aqueous layer separated was acidified with concentrated hydrochloric acid and extracted twice with ether. The combined ether extracts were subsequently washed with water and a saturated aqueous solution of sodium chloride and the solvent distilled off to give a mixture of the titled Compound A, B and C. The mixture thus obtained was used in the following reaction without purification.

We claim:
1. A tricyclic heterocyclyl compound having the following formula:

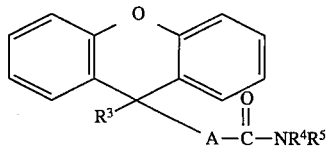

wherein,

R$^3$ represents a hydrogen atom or a lower alkyl group;

R$^4$ represents a phenyl group which has 2 substituents, wherein one of the substituents is at the 2-position and the other is at the 6-position and the substituents are individually selected from the group consisting of a lower alkyl, a lower alkoxy(lower alkyl), a lower alkylthio(lower alkyl), a lower alkoxy, a lower alkylthio, a lower alkenyl, an arylthio and a lower alkylsulfonyl;

R$^5$ represents a hydrogen atom or a lower alkyl group; and

A represents a lower alkylene group.

2. A compound according to claim 1 wherein each said substituents is selected from the group consisting of C$_1$–C$_4$alkyl, C$_1$–C$_4$alkoxy-(C$_1$–C$_4$alkyl), C$_1$–C$_4$alkylthio (C$_1$–C$_4$alkyl), C$_1$–C$_4$alkoxy, C$_1$–C$_4$alkylthio, C$_2$C$_4$alkenyl, C$_6$C$_{10}$arylthio and C$_1$–C$_4$alkylsulfonyl.

3. A compound according to claim 2 wherein the substituents are selected from the group consisting of ethyl, isopropyl, isopropylthio, methylthiomethyl, vinyl, methylthio, phenylthio, methoxymethyl, isopropoxy, and methylsulfonyl.

4. A compound according to claim 2 wherein the substituents are selected from the group consisting of methyl, ethyl, propyl, isopropyl, methoxylmethyl, methoxyethyl, ethoxymethyl, ethoxyethyl, methylthiomethyl, methylthioethyl, ethylthiomethyl, ethylthioethyl, vinyl, allyl, methoxy, ethoxy propoxy, isopropoxy, methylthio, ethylthio, propylthio, isopropylthio and phenylthio.

5. A compound according to claim 1, wherein R$^3$ represents a hydrogen atom or a methyl or ethyl group.

6. A compound according to claim 1, wherein R$^3$ represents a hydrogen atom or a methyl group.

7. A compound according to claim 1, wherein R$^5$ represents a hydrogen atom, a methyl or ethyl group.

8. A compound according to claim 1, wherein R$^5$ represents a hydrogen atom.

9. A compound according to claim 1, wherein A represents a C$_1$–C$_4$alkylene group.

10. A compound according to claim 1, wherein A represents a C$_1$–C$_2$alkylene group.

11. A compound according to claim 2, wherein:

R$^3$ represents a hydrogen atom, a methyl or ethyl group;

R$^5$ represents a hydrogen atom, a methyl or ethyl group; and

A represents a C$_1$–C$_4$alkylene group.

12. A compound according to claim 3, wherein:

R$^3$ represents a hydrogen atom, a methyl or ethyl group;

R$^5$ represents a hydrogen atom, a methyl or ethyl group; and

A represents a C$_1$–C$_4$alkylene group.

13. A compound according to claim 3, wherein:

R$^3$ represents a hydrogen atom, a methyl or ethyl group;

R$^5$ represents a hydrogen atom, a methyl or ethyl group; and

A represents a $C_1$–$C_4$alkylene group.

14. A compound according to claim 4, wherein:

$R^3$ represents a hydrogen atom or a methyl group;

$R^5$ represents a hydrogen atom; and

A represents a $C_1$–$C_2$alkylene group.

15. A compound according to claim 1, wherein:

$R^3$ represents a hydrogen atom or a methyl group;

$R^5$ represents a hydrogen atom; and

A represents a $C_1$–$C_2$alkylene group.

16. A therapeutic composition for atherosclerosis comprising a compound selected from the compounds according to claim 1 in admixture with a pharmaceutically acceptable carrier or vehicle.

17. A therapeutic composition for atherosclerosis comprising a compound selected from the compounds according to claim 11 in admixture with a pharmaceutically acceptable carrier or vehicle.

18. A therapeutic composition for atherosclerosis comprising a compound selected from the compounds according to claim 12 in admixture with a pharmaceutically acceptable carrier or vehicle.

19. A therapeutic composition for atherosclerosis comprising a compound selected from the compounds according to claim 13 in admixture with a pharmaceutically acceptable carrier or vehicle.

20. A therapeutic composition for atherosclerosis comprising a compound selected from the compounds according to claim 14 in admixture with a pharmaceutically acceptable carrier or vehicle.

21. A therapeutic composition for atherosclerosis comprising a compound selected from the compounds according to claim 15 in admixture with a pharmaceutically acceptable carrier or vehicle.

* * * * *